(12) United States Patent
Silberman et al.

(10) Patent No.: US 11,596,382 B2
(45) Date of Patent: Mar. 7, 2023

(54) METHODS AND APPARATUSES FOR ENABLING A USER TO MANUALLY MODIFY AN INPUT TO A CALCULATION PERFORMED BASED ON AN ULTRASOUND IMAGE

(71) Applicant: BFLY OPERATIONS, INC., Guilford, CT (US)

(72) Inventors: Nathan Silberman, Brooklyn, NY (US); Vineet Shah, Jersey City, NJ (US); David Elgena, Jersey City, NJ (US); David Cairns, Brooklyn, NY (US); Elizabeth Lauer, Campbell, CA (US); Cristina Shin, San Francisco, CA (US)

(73) Assignee: BFLY OPERATIONS, INC., Guilford, CT (US)

( * ) Notice: Subject to any disclaimer, the term of this patent is extended or adjusted under 35 U.S.C. 154(b) by 374 days.

(21) Appl. No.: 16/793,841

(22) Filed: Feb. 18, 2020

(65) Prior Publication Data

US 2020/0261054 A1    Aug. 20, 2020

Related U.S. Application Data

(60) Provisional application No. 62/807,087, filed on Feb. 18, 2019.

(51) Int. Cl.
*G06F 3/04847*    (2022.01)
*G06F 3/04845*    (2022.01)
(Continued)

(52) U.S. Cl.
CPC .......... *A61B 8/0883* (2013.01); *A61B 8/463* (2013.01); *A61B 8/465* (2013.01); *A61B 8/469* (2013.01);
(Continued)

(58) Field of Classification Search
CPC ....... A61B 8/0883; A61B 8/463; A61B 8/465; A61B 8/469; A61B 8/5223;
(Continued)

(56) References Cited

U.S. PATENT DOCUMENTS

| 6,447,454 B1 | 9/2002 | Chenel et al. |
| 2005/0020917 A1* | 1/2005 | Scherch ............... A61N 5/1049 |
| | | 600/437 |

(Continued)

FOREIGN PATENT DOCUMENTS

| WO | WO 2017/222964 A1 | 12/2017 |
| WO | WO 2017/222970 A1 | 12/2017 |

OTHER PUBLICATIONS

International Search Report and Written Opinion dated May 22, 2020 in connection with International Application No. PCT/US2020/018626.

(Continued)

*Primary Examiner* — Jennifer N Welch
*Assistant Examiner* — Ashley M Fortino
(74) *Attorney, Agent, or Firm* — Carter, DeLuca & Farrell LLP

(57) ABSTRACT

Aspects of the technology described herein relate to methods and apparatuses for enable a user to manually modify an input to a calculation performed based at least in part on an ultrasound image. In some embodiments, manually modifying the input comprises manually modifying a trace on the image. In some embodiments, manually modifying the input comprises manually selecting an ultrasound image from a series of ultrasound images on which a calculation is to be performed.

11 Claims, 29 Drawing Sheets

(51) Int. Cl.
*G06F 3/04817* (2022.01)
*G06F 3/04842* (2022.01)
*G06F 3/0485* (2022.01)
*A61B 8/08* (2006.01)
*A61B 8/00* (2006.01)

(52) U.S. Cl.
CPC ...... *G06F 3/04845* (2013.01); *G06F 3/04847* (2013.01); *G06F 3/0485* (2013.01); *G06F 3/04817* (2013.01); *G06F 3/04842* (2013.01)

(58) Field of Classification Search
CPC ............. G06F 3/04845; G06F 3/04847; G06F 3/04817; G06F 3/04842; G06F 3/0485
See application file for complete search history.

(56) References Cited

U.S. PATENT DOCUMENTS

| | | | | |
|---|---|---|---|---|
| 2007/0255136 | A1* | 11/2007 | Kristofferson | A61B 8/145 600/437 |
| 2008/0009733 | A1* | 1/2008 | Saksena | A61B 5/411 600/443 |
| 2008/0170765 | A1* | 7/2008 | D'sa | G06T 7/12 382/128 |
| 2011/0055447 | A1 | 3/2011 | Costa | |
| 2014/0164965 | A1* | 6/2014 | Lee | A61B 8/467 715/765 |
| 2016/0093044 | A1* | 3/2016 | Okazaki | G06T 7/0016 382/131 |
| 2016/0113626 | A1 | 4/2016 | Lee et al. | |
| 2016/0228091 | A1 | 8/2016 | Chiang et al. | |
| 2016/0331469 | A1* | 11/2016 | Hall | A61B 8/0841 |
| 2017/0193658 | A1 | 7/2017 | Cardinal et al. | |
| 2017/0360397 | A1 | 12/2017 | Rothberg et al. | |
| 2017/0360401 | A1 | 12/2017 | Rothberg et al. | |
| 2018/0210632 | A1 | 7/2018 | Schmied et al. | |
| 2019/0142388 | A1 | 5/2019 | Gonyeau et al. | |
| 2019/0196600 | A1 | 6/2019 | Rothberg et al. | |
| 2019/0282208 | A1 | 9/2019 | Silberman et al. | |
| 2019/0307428 | A1 | 10/2019 | Silberman et al. | |
| 2020/0037986 | A1 | 2/2020 | Silberman et al. | |
| 2020/0037987 | A1 | 2/2020 | Silberman et al. | |
| 2020/0046322 | A1 | 2/2020 | Silberman | |
| 2020/0054307 | A1 | 2/2020 | Silberman et al. | |
| 2020/0214672 | A1 | 7/2020 | de Jonge et al. | |
| 2020/0214674 | A1 | 7/2020 | Gafner et al. | |
| 2020/0214679 | A1 | 7/2020 | Silberman et al. | |

OTHER PUBLICATIONS

PCT/US2020/018626, May 22, 2020, International Search Report and Written Opinion.
PCT/US2020/018626, Aug. 26, 2021, International Preliminary Report on Patentability.
International Preliminary Report on Patentability for International Application No. PCT/US2020/018626, dated Aug. 26, 2021.

* cited by examiner

METHODS AND APPARATUSES FOR ENABLING A USER TO MANUALLY MODIFY AN INPUT TO A CALCULATION PERFORMED BASED ON AN ULTRASOUND IMAGE

CROSS-REFERENCE TO RELATED APPLICATIONS

The present application claims the benefit under 35 U.S.C. § 119(e) of U.S. Patent Application Ser. No. 62/807,087, filed Feb. 18, 2019 and entitled "METHODS AND APPARATUSES FOR MODIFYING AUTOMATIC MEASUREMENTS ON ULTRASOUND IMAGES," which is hereby incorporated herein by reference in its entirety.

FIELD

Generally, the aspects of the technology described herein relate to collection of ultrasound data. Some aspects relate to methods and apparatuses for modifying calculations on ultrasound images.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the present application, an apparatus is provided, comprising a processing device configured to enable a user to manually modify an input to a calculation performed based at least in part on an ultrasound image, wherein the input comprises definition of a trace on the ultrasound image or selection of the ultrasound image from a series of ultrasound images.

In some embodiments, the processing device is configured, when enabling the user to manually modify the input to the calculation, to: display the ultrasound image, the trace superimposed on the ultrasound image, and an icon adjacent to the trace; in response to detecting a dragging movement that begins on or within a threshold distance of the icon, scale the trace by an amount corresponding to a component of a distance covered by the dragging movement along a long axis of the trace, and rotate the trace by an amount corresponding to a component of the distance covered by the dragging movement perpendicular to the long axis of the trace; and perform the calculation based on the manually modified trace.

In some embodiments, the processing device is configured, when enabling the user to manually modify the input to the calculation, to: display the ultrasound image, the trace superimposed on the ultrasound image, and an icon adjacent to the trace; in response to detecting a dragging movement that begins on or within a threshold distance of the icon, translate the trace by an amount in a horizontal direction corresponding to a component of a distance covered by the dragging movement in the horizontal direction, and translate the trace by an amount in a vertical direction corresponding to a component of the distance covered by the dragging movement in the vertical direction; and perform the calculation based on the manually modified trace.

In some embodiments, the processing device is configured, when enabling the user to manually modify the input to the calculation, to: display the ultrasound image, the trace superimposed on the ultrasound image, and an icon adjacent to the trace; in response to detecting a dragging movement that begins on or within a threshold distance of the icon, reposition the point at a new location based on the dragging movement and redraw the trace such that the trace extends through the new location of the point; and perform the calculation based on the manually modified trace.

According to an aspect of the present application, a method is provided, comprising enabling, with a processing device, a user to manually modify an input to a calculation performed based at least in part on an ultrasound image, wherein the input comprises definition of a trace on the ultrasound image or selection of the ultrasound image from a series of ultrasound images.

In some embodiments, the method further comprises: displaying the ultrasound image, the trace superimposed on the ultrasound image, and an icon adjacent to the trace; in response to detecting a dragging movement that begins on or within a threshold distance of the icon, scaling the trace by an amount corresponding to a component of a distance covered by the dragging movement along a long axis of the trace, and rotating the trace by an amount corresponding to a component of the distance covered by the dragging movement perpendicular to the long axis of the trace; and performing the calculation based on the manually modified trace.

In some embodiments, the method further comprises: displaying the ultrasound image, the trace superimposed on the ultrasound image, and an icon adjacent to the trace; in response to detecting a dragging movement that begins on or within a threshold distance of the icon, translating the trace by an amount in a horizontal direction corresponding to a component of a distance covered by the dragging movement in the horizontal direction, and translating the trace by an amount in a vertical direction corresponding to a component of the distance covered by the dragging movement in the vertical direction; and performing the calculation based on the manually modified trace.

Some aspects include at least one non-transitory computer-readable storage medium storing processor-executable instructions that, when executed by at least one processor, cause the at least one processor to perform the above aspects. Some aspects include a method of performing the above aspects.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear

DETAILED DESCRIPTION

Figure 1:
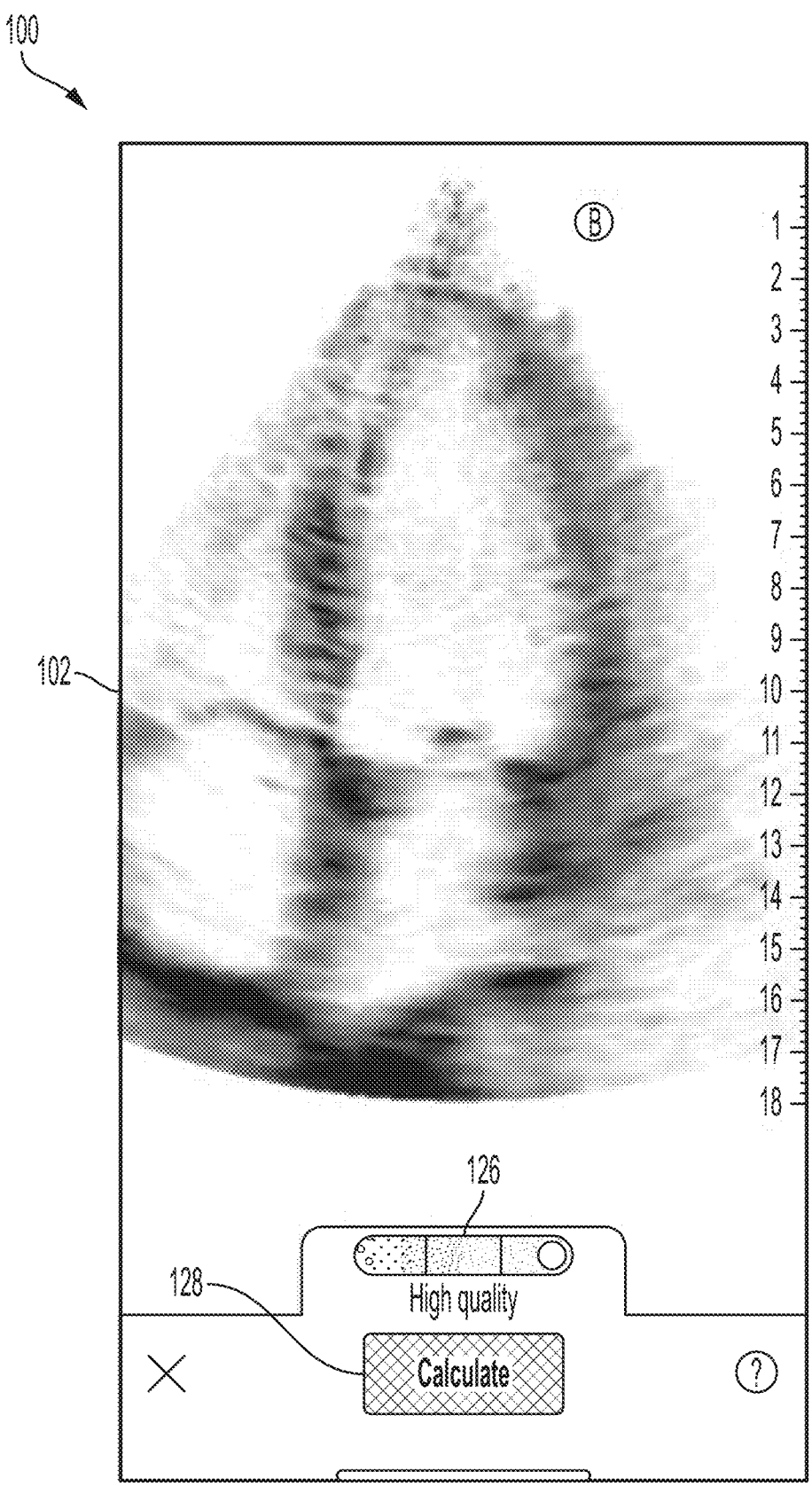
FIG. 1 illustrates an example graphical user interface (GUI) in accordance with certain embodiments described herein.

Advances in artificial intelligence technology have enabled performance of automatic calculations on ultrasound images, potentially obviating the need for operators to have the required knowledge for manually performing such calculations. Aspects of such automatic calculations are described in U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1, which is incorporated by reference herein in its entirety. As an example, calculations of ejection fraction may be based on calculations of areas within traces drawn on ultrasound images. Such traces may be drawn automatically using artificial intelligence, but users may wish to modify the traces in order to modify the resulting calculation value.

The inventors have developed technology for assisting a user in modifying traces on ultrasound images depicted by the touch-sensitive display screen of a processing device. The technology includes displaying a trace superimposed on the ultrasound image, a first icon adjacent to the trace, and a second icon adjacent to the trace. Based on a dragging movement that begins at the first icon, the trace may be scaled and/or rotated. Based on a dragging movement that begins at the second icon, the trace may be translated. A calculation may be performed based on the trace. Generally, the technology may include using a certain number of regions of the touch-sensitive display screen to control more degrees of freedom of the trace than the number of regions. For example, two icons adjacent to the trace may control three degrees of freedom of the box: scaling, rotation, and positioning. This technology may provide a means of flexibly modifying traces that avoids excessively complicated selections of options on the touch-sensitive display screen and excessive crowding of the touch-sensitive display screen with controls.

A point on the trace and a cursor adjacent to the point may also be displayed. The cursors may maintain a fixed distance away from the point. Based on a dragging movement that begins at the cursor, the point may be repositioned at a new location based on the dragging movement and the trace may be redrawn such that the trace extends through the new location of the point. A calculation may be performed based on the trace. Because the cursor may be a fixed distance away from the point that is repositioned, the point may be removed from the user's finger by the fixed distance as the user contacts the cursors and drags his/her finger across the touch-sensitive display screen. Thus, as the user drags his/her finger, the point may be visible to the user, and the user may be able to determine when the point has moved to the desired location and release his/her finger from the touch-sensitive display to cause the point to remain in the desired location. In addition to modifying traces, the inventors have developed technology for assisting a user in modifying selection of which images in a series are selected for use in calculations such as ejection fraction calculation.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

While the description below includes certain methods that a processing device may use to cause a given result to occur, a processing device may implement different methods in order to cause the same result to occur. In particular, code designed to cause the result to occur may implement a different method to cause the result to occur than those described.

FIGS. 1-3 and 7-23 illustrate examples graphic user interfaces (GUIs) that may be displayed by a processing device in an ultrasound system. The processing device may be, for example, a mobile phone, tablet, or laptop. The processing device may be in operative communication with an ultrasound device, and the ultrasound device and the processing device may communicate over a wired communication link (e.g., over Ethernet, a Universal Serial Bus (USB) cable or a Lightning cable) or over a wireless communication link (e.g., over a BLUETOOTH, WiFi, or ZIGBEE wireless communication link). In some embodiments, the ultrasound device itself may display the GUIs.

FIG. 1 illustrates an example graphical user interface (GUI) 100 in accordance with certain embodiments described herein. The GUI 100 includes an ultrasound image 102, a quality indicator 126, and an automatic calculation option 128.

The ultrasound image 102 may be generated based on raw ultrasound data collected by the ultrasound device. In FIG. 1 and the other figures included herein, the ultrasound images are shown in black and white. Those colors may be reversed in practice, meaning that regions shown in white may alternatively be shown in black, and vice versa. For ease of illustration of some of the surrounding structures shown in later figures, white is shown as the background color in the ultrasound image 102. In practice, black may be the background color and the additional structures shown in later figure may be shown in color in some embodiments.

In some embodiments, the ultrasound device may generate the ultrasound image 102 based on the raw ultrasound data and transmit the ultrasound image 102 to the processing device. In some embodiments, the ultrasound device may generate scan lines from the raw ultrasound data, transmit the scan lines to the processing device, and the processing device may generate the ultrasound image 102 from the scan lines. In some embodiments, the ultrasound device may transmit the raw ultrasound data to the processing device and the processing device may generate the ultrasound image 102 from the raw ultrasound data. Generally, collecting an ultrasound image by an ultrasound device may mean collecting ultrasound data from which the ultrasound image is generated. The processing device may update the GUI 100 with new ultrasound images 102 as the ultrasound device collects new ultrasound data. In this description, for simplicity, any ultrasound image currently shown in a GUI will be referred to as the ultrasound image 102, even if the particular ultrasound image 102 shown in one GUI may be different than the particular ultrasound image 102 shown in a different GUI.

The quality indicator 126 may generally indicate a quality of the ultrasound image 102 and previously collected ultrasound images for the purpose of automatically performing a calculation. The following description focuses on calculation of ejection fraction, although other calculations may be performed as well. The processing device may automatically determine the quality. For further description of determining the quality of ultrasound images, see U.S. Provisional Patent Application No. 62/851,502 titled "METHODS AND APPARATUSES FOR ANALYZING IMAGING DATA," filed on May 22, 2019 (and assigned to the assignee of the instant application), which is incorporated by reference herein in its entirety.

In some embodiments, upon receiving a selection from a user of the automatic calculation option 128, the processing device may record a series of ultrasound images to a buffer. If the quality of the series of ultrasound images for the purpose of performing the automatic calculation exceeds a threshold, in some embodiments the processing device may proceed with performing the automatic calculation and then display the GUI 200. In some embodiments, the processing device may also display the GUI 200 based on receiving a selection to perform the automatic calculation on ultrasound images previously saved to memory. If the quality of the series of ultrasound images for performing the automatic calculation does not exceed the threshold, in some embodiments the processing device may display the GUI 2000.

Ejection fraction may be calculated based on a series of ultrasound images from the heart using the modified Simpson's formula. The modified Simpson's formula uses two ultrasound images of the heart from the series, one ultrasound image depicting a four-chamber apical view of the heart at end-diastole of a heartbeat and one ultrasound image depicting a four-chamber apical view of the heart at end-systole of the heartbeat. Areas within traces of the endocardial border of the left ventricle in the end-diastolic ultrasound image and the end-systolic ultrasound image may be used to calculate end-diastolic volume ($V_{ED}$) and end-systolic volume ($V_{ES}$), respectively, by splitting the area within each trace into thin sections, assuming each sections represents a cross-section of a three-dimensional disc, and summing the volumes of the disks to calculate a volume. Ejection fraction may then be calculated as $(V_{ED}-V_{ES})/V_{ED} \times 100$.

In some embodiments, when automatically calculating ejection fraction, the processing device may use a statistical model to automatically select ultrasound images from the series of ultrasound images as the end-diastolic ultrasound image and the end-systolic ultrasound image. Additionally, the processing device may use a statistical model to automatically generate traces of the endocardial border of the left ventricles in the end-diastolic ultrasound image and the end-systolic ultrasound image. The automatically-generated traces from the automatically-selected end-diastolic ultrasound image and end-systolic ultrasound image may be used to calculate an initial value for ejection fraction using the formula described above. The processing device may display the GUI 200 after the processing device automatically calculates the initial value for ejection fraction.

This description describes GUIs a user may use to manually modify the ejection fraction calculation that was initially calculated automatically by the statistical model. In particular, the user may modify which ultrasound images from the series of ultrasound images are selected as the end-diastolic ultrasound image and the end-systolic ultrasound image (i.e., different from what the statistical model initially selected). Additionally, the user may modify the traces of the endocardial border of the left ventricles that are automatically generated by the statistical model for the end-diastolic ultrasound image and the end-systolic ultrasound image. For example, a user may modify the traces generated automatically by the statistical model for the end-diastolic ultrasound image and the end-systolic ultrasound image automatically selected by the statistical model. As another example, a user may modify the traces generated automatically by the statistical model for the end-diastolic ultrasound image and the end-systolic ultrasound image manually selected by the users. The traces (which may be manually modified) from the end-diastolic ultrasound image and the end-systolic ultrasound image (which may be manually selected) may be used to calculate a new value for ejection fraction using the formula described above. The processing device may also display the GUI 200 after the processing device recalculates a value for ejection fraction based on the user's manual modifications to the selections of the end-diastolic ultrasound image and the end-systolic ultrasound image and/or after the traces on these ultrasound images. Generally, this description describes GUIs a user may use to manually modify inputs to a calculation based, at least in part, on one or more ultrasound images. In some embodiments, the GUIs may enable the user to manually modify the inputs to the calculation after the processing device has performed an initial automatic calculation. In some embodiments, the GUIs may enable the user to manually modify the inputs to the calculation before the calculation has been performed at all. In some embodiments, the inputs may include selection of one or more particular ultrasound images from a series and/or definition of traces on one or more ultrasound images.

Figure 2:
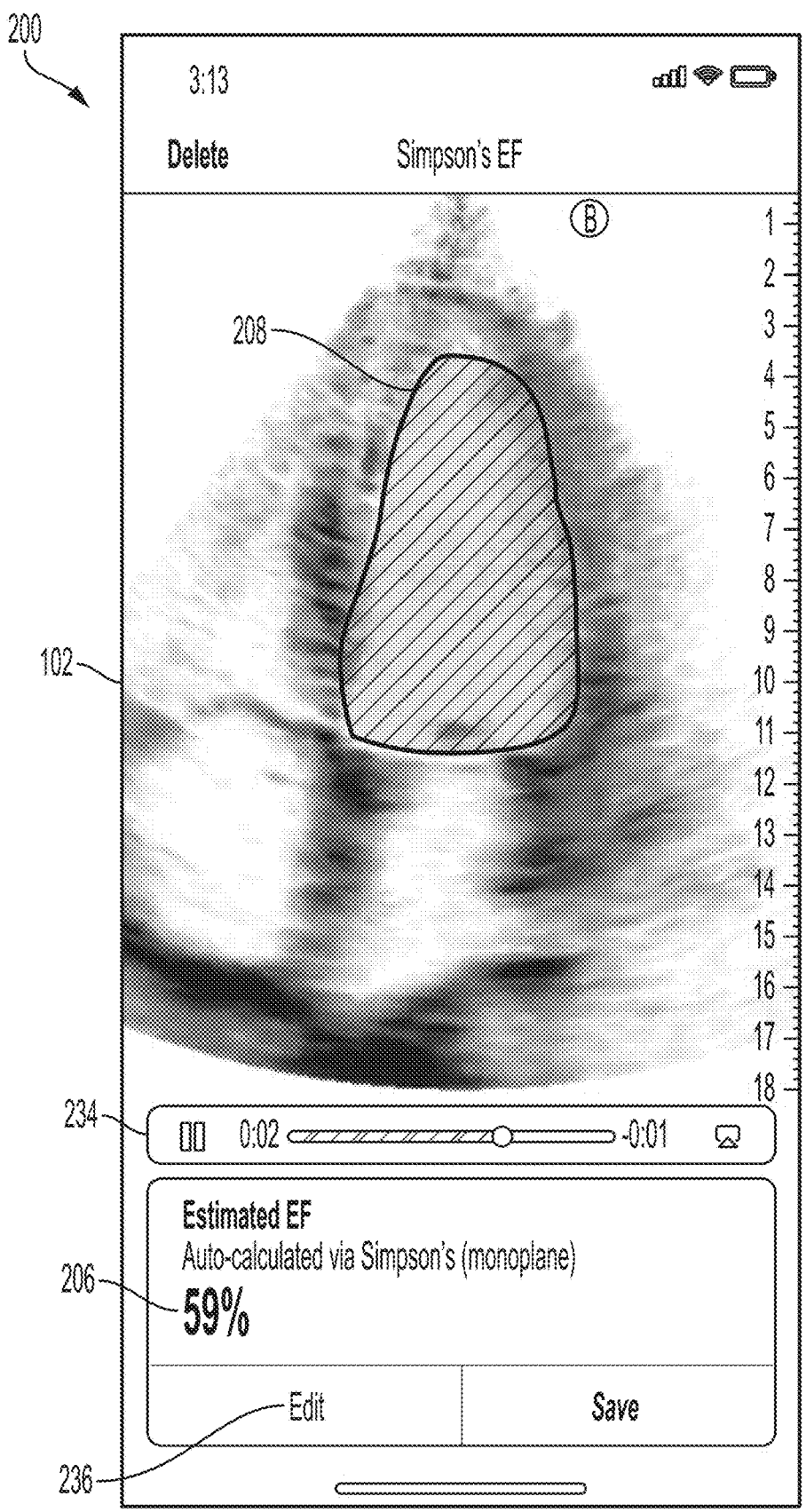
FIG. 2 illustrates an example GUI in accordance with certain embodiments described herein.

FIG. 2 illustrates an example GUI 200 in accordance with certain embodiments described herein. The GUI 200 includes an ultrasound image 102 from a series of ultrasound images, a trace 208, an automatic calculation value 206, a cine control and information bar, and an edit option 236.

The GUI 200 displays the series of ultrasound images as a cine, and may display the cine on loop. The cine control and information bar 234 may enable a user to control display of the cine (e.g., stopping and starting). The cine control and information bar 234 may also display information about the cine, such as the time length of the cine and the position in time within the cine of the ultrasound image 102 currently displayed. When the current ultrasound image displayed in the cine is the end-diastolic ultrasound image or the end-systolic ultrasound image (selected either automatically or manually), the GUI 200 may display the trace of the endocardial border of the left ventricle in the ultrasound image (either generated automatically or manually) superimposed on the ultrasound image. Thus, in FIG. 2, the ultrasound image 102 may be the end-diastolic ultrasound image or the end-systolic ultrasound image, and a trace 208 of the endocardial border of the left ventricle in the ultrasound image 102 is superimposed on the ultrasound image 102. The processing device may automatically generate the trace 208 using a statistical model. In this description, for simplicity, any trace generated for the ultrasound image 102 currently displayed in a GUI will be referred to as the trace 208, even if the particular ultrasound image 102 and trace 208 displayed in one GUI may be different than the particular ultrasound image 102 and trace 208 displayed in a different GUI.

The automatic calculation value 206 depicts the value for ejection fraction as calculated based on $V_{ED}$ and $V_{ES}$, which are calculated from the traces (whether automatically generated or manually modified) on the end-diastolic and end-systolic ultrasound images in the series of ultrasound images (whether automatically or manually selected). If the end-diastolic and end-systolic ultrasound images are selected automatically by a statistical model and the traces on the end-diastolic and end-systolic ultrasound images are generated automatically by a statistical model, the automatic calculation value 206 may depict a value for ejection fraction that is calculated completely automatically. If a user has modified the selections of the end-diastolic and end-systolic ultrasound images and/or the traces on these ultrasound images, the value for ejection value may be modified from the automatically-calculated value based on the user modifications. In non-ejection fraction contexts, the automatic calculation value 206 may depict the value for the particular calculation being performed.

A user may manually modify the selections for the end-diastolic and end-systolic ultrasound images and/or the traces on these ultrasound images, and thereby modify the ejection fraction value, by selecting the edit option 236. Upon receiving a selection of the edit option 236, the processing device may display the GUI 300. Generally, in non-ejection fraction contexts, the edit option 236 may enable a user to modify inputs to the calculation, where the inputs may include selection of one or more particular ultrasound images from a series and/or definition of traces on one or more ultrasound images.

Figure 3:
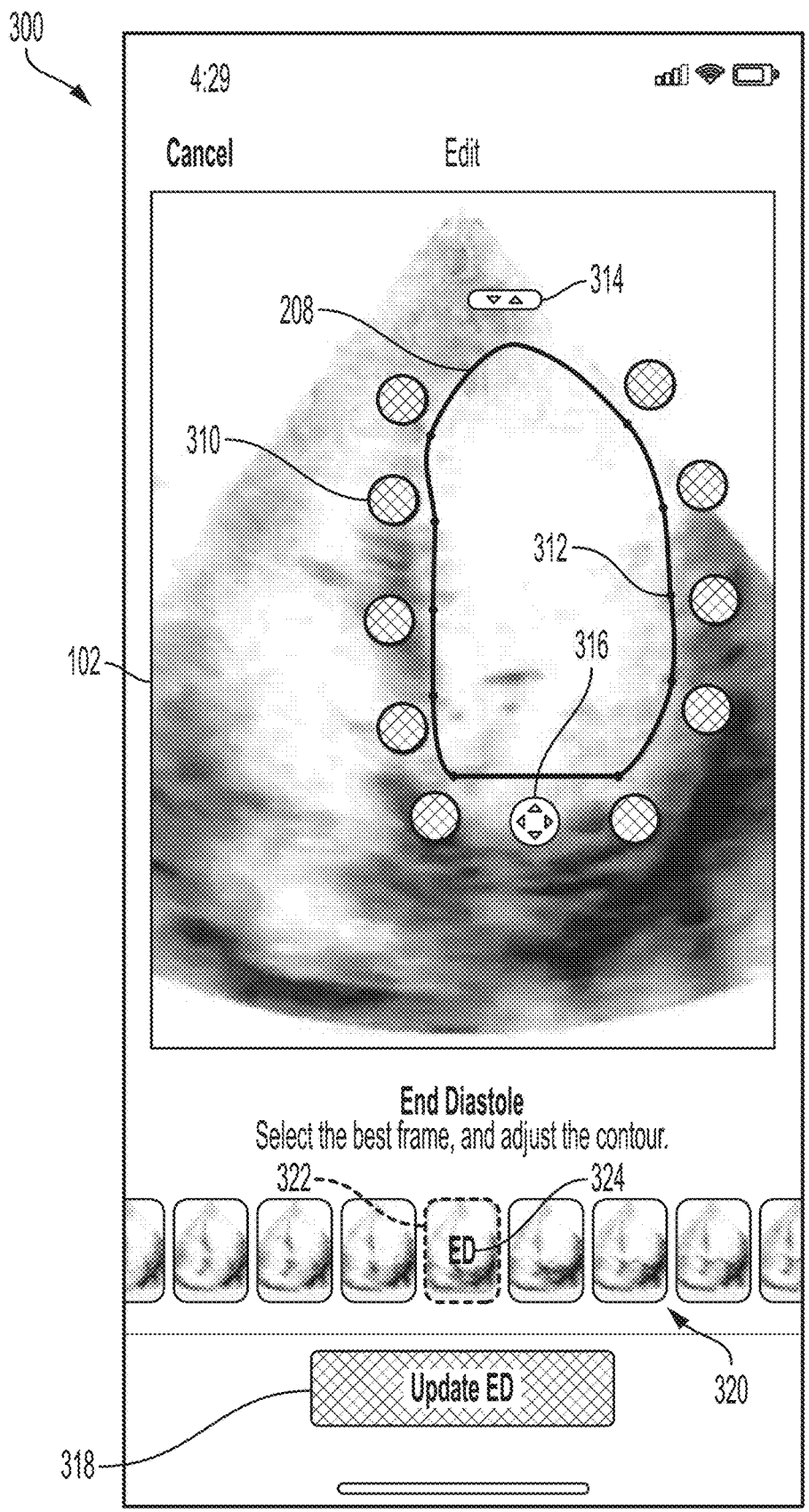
FIG. 3 illustrates an example GUI, in accordance with certain embodiments described herein.

FIG. 3 illustrates an example GUI 300, in accordance with certain embodiments described herein. From the GUI 300, the user may manually modify the selections of the end-diastolic and end-systolic ultrasound images and/or manually modify the traces of the endocardial border of the left ventricle in these ultrasound images. As described above, the processing device may display the GUI 300 in response to selection of the edit option 236 from the GUI 200.

The GUI 300 includes an ultrasound image 102, a trace 208, cursors 310, points 312, a first icon 314, a second icon 316, an end-diastolic ultrasound image update option 318, ultrasound image thumbnails 320, a current ultrasound image indicator 322, and an end-diastolic ultrasound image indicator 324.

The ultrasound image 102 in the GUI 300 is the ultrasound image currently selected (either automatically by a statistical model or manually by a user) as the end-diastolic ultrasound image. While this description describes the processing device presenting the end-diastolic ultrasound image and then the end-systolic ultrasound image, in some embodiments the processing device may present the end-systolic ultrasound image and then the end-diastolic ultrasound image. The trace 208 traces the endocardial border of the left ventricle in the ultrasound image 102. The processing device may use a statistical model to automatically generate the trace 208. In FIG. 3, the area within the trace 208 is not filled in. However, in some embodiments, the trace 208 may be filled in. The points 312 are located on the trace 208. Further description of determining the locations of the points 312 may be found with reference to FIG. 4. It should be appreciated that in FIG. 3, only one of the points 312 is labeled with a reference numeral, but all the matching points on the trace 208 are among the points 312. Each point 312 has a corresponding cursor 310 that is adjacent to and located a fixed distance (e.g., a fixed number of pixels) away from the point 312. It should be appreciated that in FIG. 3, only one of the cursors 310 is labeled with a reference numeral, but all the matching cursors next to the trace 208 are among the cursors 310. Further description of determining the locations of the cursors 310 may be found with reference to FIG. 5.

The ultrasound image thumbnails 320 depict thumbnail images of ultrasound images in the series of ultrasound images of which the ultrasound image 102 is a part. Ultrasound image thumbnails for all the ultrasound images in the series may not fit in the GUI 300 at once. The processing device may scroll left or right through the ultrasound image thumbnails 320 in response to receiving a left or right swipe from the user on the ultrasound image thumbnails 320. The end-diastolic ultrasound image indicator 324 is superimposed on the ultrasound image thumbnail 320 corresponding to the ultrasound image currently selected (either automatically or manually) for end-diastole. In FIG. 3, the end-diastolic ultrasound image indicator 324 includes the text "ED" (abbreviation for end-diastole), although other text and/or symbols may be used. Further description of using the ultrasound image thumbnails 320 to modify selection of the end-diastolic ultrasound image may be found with reference to FIG. 17.

Figure 4:
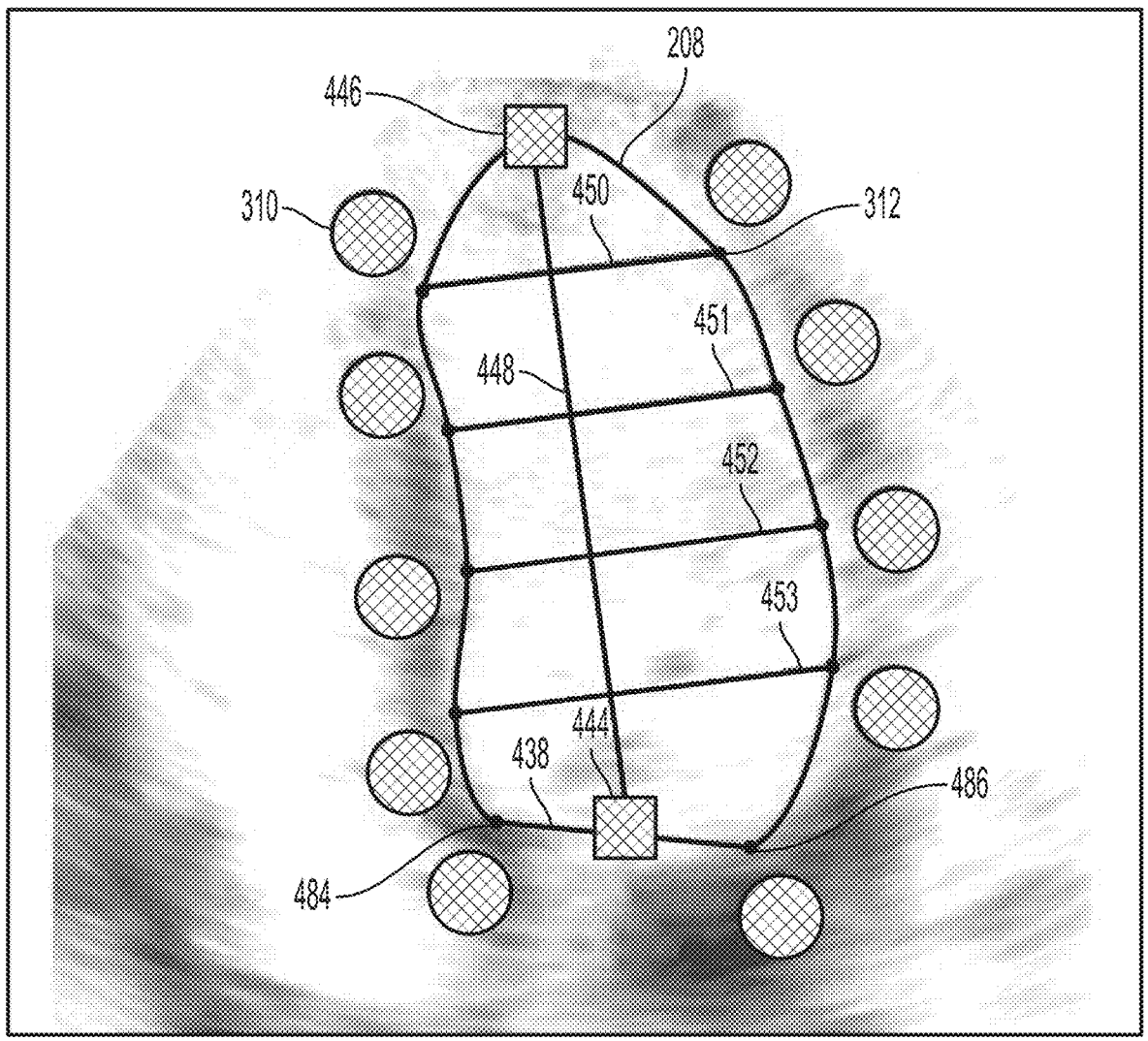
FIG. 4 illustrates a method for determining the locations of points on a trace, in accordance with certain embodiments described herein.

FIG. 4 illustrates a method for determining the locations of the points 312 on the trace 208, in accordance with certain embodiments described herein. It should be appreciated that in FIG. 4, only one of the points 312 is labeled with a reference numeral, but all the matching points on the trace 208 are among the points 312. In the embodiment of FIG. 4, the trace 208 includes a linear base portion 438 extending between two endpoints 484 and 486, each of which is one of the points 312. The base portion 438 includes a midpoint 444. The trace 208 also includes an apex 446. In this embodiment, the statistical model that generates the trace 208 may return the locations of the endpoints 484 and 486 of the base portion 438, the location of the apex 446, and multiple points along the trace 208 between the apex 446 and each of the endpoints 484 and 486. The processing device may determine a long axis 448 of the trace 208 that extends from the midpoint 444 to the apex 446. The processing device may determine four short axes 450, 451, 452, and 453 of the trace 208, each of which is perpendicular to the long axis 448, and which divide the long axis 448 into six equal segments. The processing device may determine the remaining points 312 (namely, those aside from the endpoints 484 and 486) to be the points of intersection between the short axes 450-453 and the trace 208. It should be appreciated that while four short axes 450-453 are used, other numbers of short axes may be used (e.g., 2, 3, 5, 6, etc.), resulting in fewer or more points 312. It should be appreciated that while FIG. 4 includes a marker at the apex 446, a marker at the midpoint 444, the long axis 448, and the short axes 450-453, these are illustrative and may not be actually displayed by the processing device. It should be appreciated that FIG. 4 is non-liming and other methods for determining the locations of the points 312 may be used.

Figure 5:
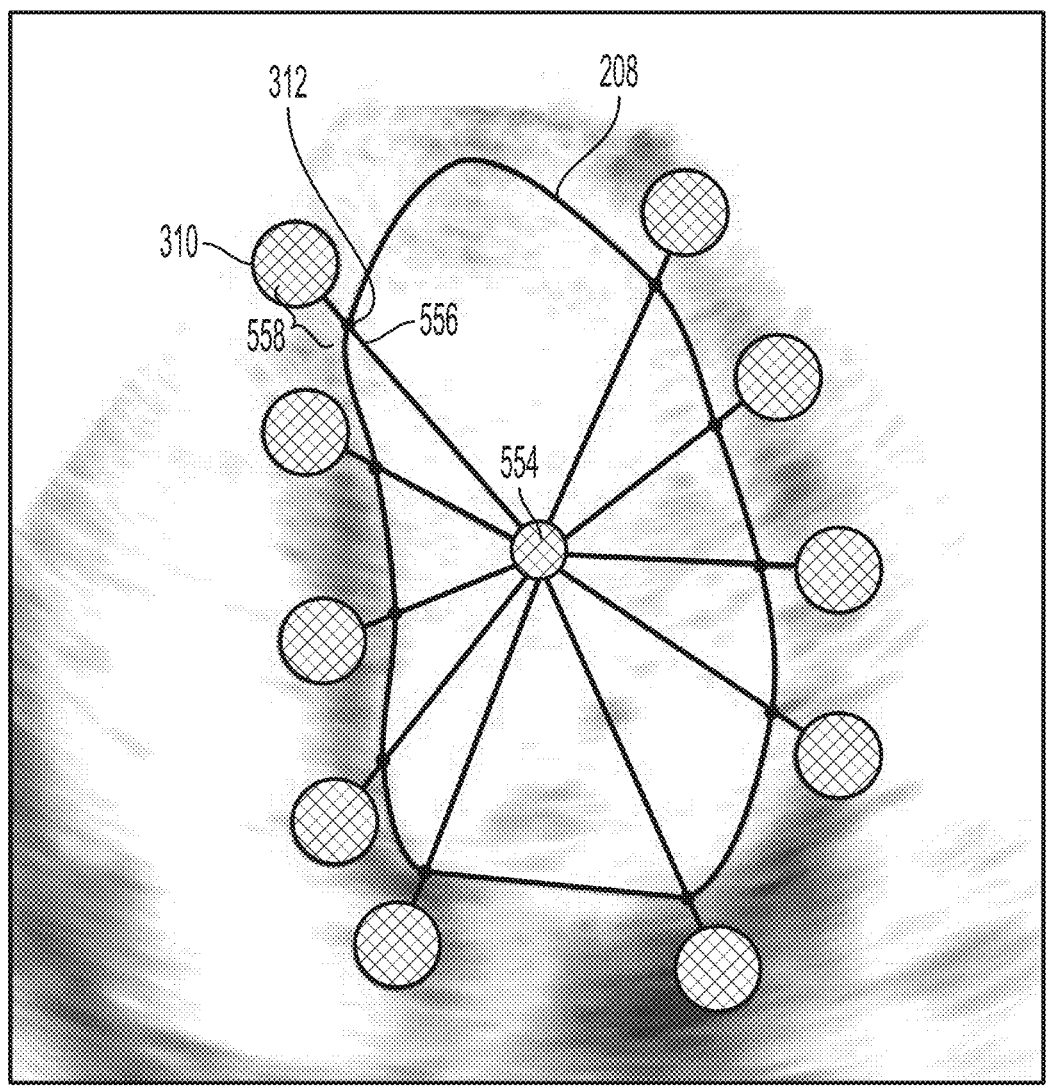
FIG. 5 illustrates a method for determining the location of a cursor relative to a point on a trace, in accordance with certain embodiments described herein.

FIG. 5 illustrates a method for determining the location of a cursor 310 relative to the point 312 on the trace 208, in accordance with certain embodiments described herein. FIG. 5 illustrates the centroid 554 of the area within the trace 208. The cursor 310 is located a fixed distance 558 outside the trace 208 along a line 556 defined by the centroid 554 and the point 312. It should be appreciated that this same method may be used to determine the locations of all the cursors 310 around the trace 208. It should also be appreciated that FIG. 5 is non-liming and other methods for determining the locations of the cursors 310 may be used.

Figure 6:
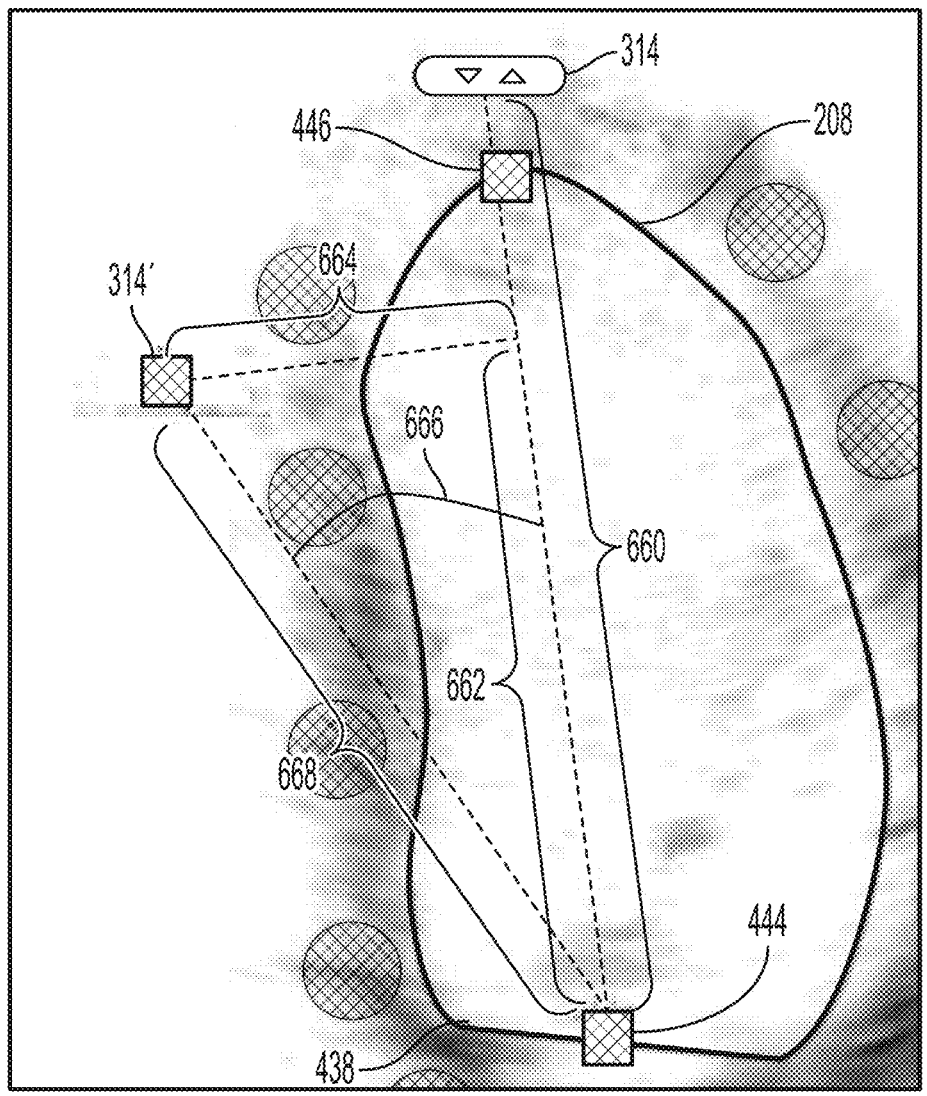
FIG. 6 illustrates a method for determining how to rotate and/or scale a trace based on a dragging movement that begins on or within a threshold distance of an icon, in accordance with certain embodiments described herein.

As described above, the area within the trace 208 may be used to calculate end-diastolic volume ($V_{ED}$), which is used to calculate ejection fraction, by splitting the area within the trace 208 into thin sections, assuming each sections represents a cross-section of a three-dimensional disc, and summing the disks to calculate a volume. This description describes GUIs that a user may use to manually modify the trace 208, including methods using the first icon 314, the second icon 316, and the cursors 310, and thereby modify the ejection fraction value. Returning to FIG. 3, in some embodiments, the processing device may rotate and/or scale the trace 208 based on a dragging movement across a touch-sensitive display screen that begins on or within a threshold distance (e.g., 30 pixels) of the first icon 314. FIG. 6 illustrates a method for determining how to rotate and/or scale the trace 208 based on a dragging movement that begins on or within a threshold distance of the first icon 314, in accordance with certain embodiments described herein. FIG. 6 illustrates the first icon 314 at an old position (labeled as 314) and the trace 208 at an old position. FIG. 6 also illustrates the end position 314' of a dragging movement that begins at or within a threshold distance of the first icon 314.

The processing device may determine (1) a line 660 that extends between the old position of the first icon 314 and the midpoint 444 of the base portion 438 of the trace 208. The first icon 314 is located outside the trace 208 a fixed distance away from the apex 446 along the line 660; (2) a line 664 that extends from the end position 314' of the dragging movement to the line 660 and is perpendicular to the line 660; (3) a portion 662 of the line 660 that is between the midpoint 444 and the line 664; (4) a line 668 that extends between the end position 314' of the dragging movement and the midpoint 444; and (5) an angle 666 between the line 660 and the line 668. In some embodiments, in response to a dragging movement from 314 to 314', the processing device may scale the height and width of the trace 208 by the ratio of the length of the portion 662 of the line 660 to the total length of the line 660.

In some embodiments, the processing device may scale the height and width of the trace 208 about the midpoint 444. For example, if the location of the midpoint 444 is (mx, my), and the scaling factor is f, the processing device may scale a given point on the trace 208 at (x, y) to (f*(x−mx)+mx, f*(y−my)+my. In some embodiments, the processing device may scale the trace 208 about other points as (e.g., the centroid or the apex of the trace 208). In some embodiments, only the height of the trace 208 may be scaled by the ratio of the length of the portion 662 of the line 660 to the total length of the line 660, while the width of the trace 208 may stay the same. The height of the trace 208 may be the dimension of the trace 208 along the line 660 and the width of the trace 208 may be the dimension of the trace 208 that is perpendicular to the line 660.

In some embodiments, the processing device may rotate the trace 208 by the angle 666. In some embodiments, the processing device may rotate the height and width of the trace 208 about the midpoint 444. For example, if the location of the midpoint 444 is (mx, my), and the rotation angle 666 is referred to as θ, the processing device may rotate a given point on the trace 208 at (x,y) to ((x−mx) cos θ−(y−my) sin θ+mx, (x−mx) sin θ+(y−my) cos θ+my).

In other words, an arbitrary dragging movement that begins on or within a threshold distance of the first icon 314 may have a component in a direction along a long axis of the trace 208 (i.e., along the line 660 between the midpoint 444 of the base portion 438 of the trace 208) and a component in a direction perpendicular to the long axis of the trace 208. The processing device may scale the trace 208 based on the component of the dragging movement that is along the long axis of the trace 208. The processing device may rotate the trace 208 based on the component of the dragging movement that is perpendicular to the long axis of the trace 208.

In some embodiments, rather than measuring the line 660 between the old position of the first icon 314 and the midpoint 444, the line 660 may extend from the apex 446 to the midpoint 444.

While the above description has described a trace 208 having a linear base portion, in some embodiments the trace 208 may have other shapes. For example, the trace 208 may be an ellipse. The long axis 448 and the line 660 may then correspond to the major axis of the ellipse. It should be appreciated that FIG. 6 is non-liming and other methods for determining how to scale and rotate the trace 208 may be used.

Figure 7:
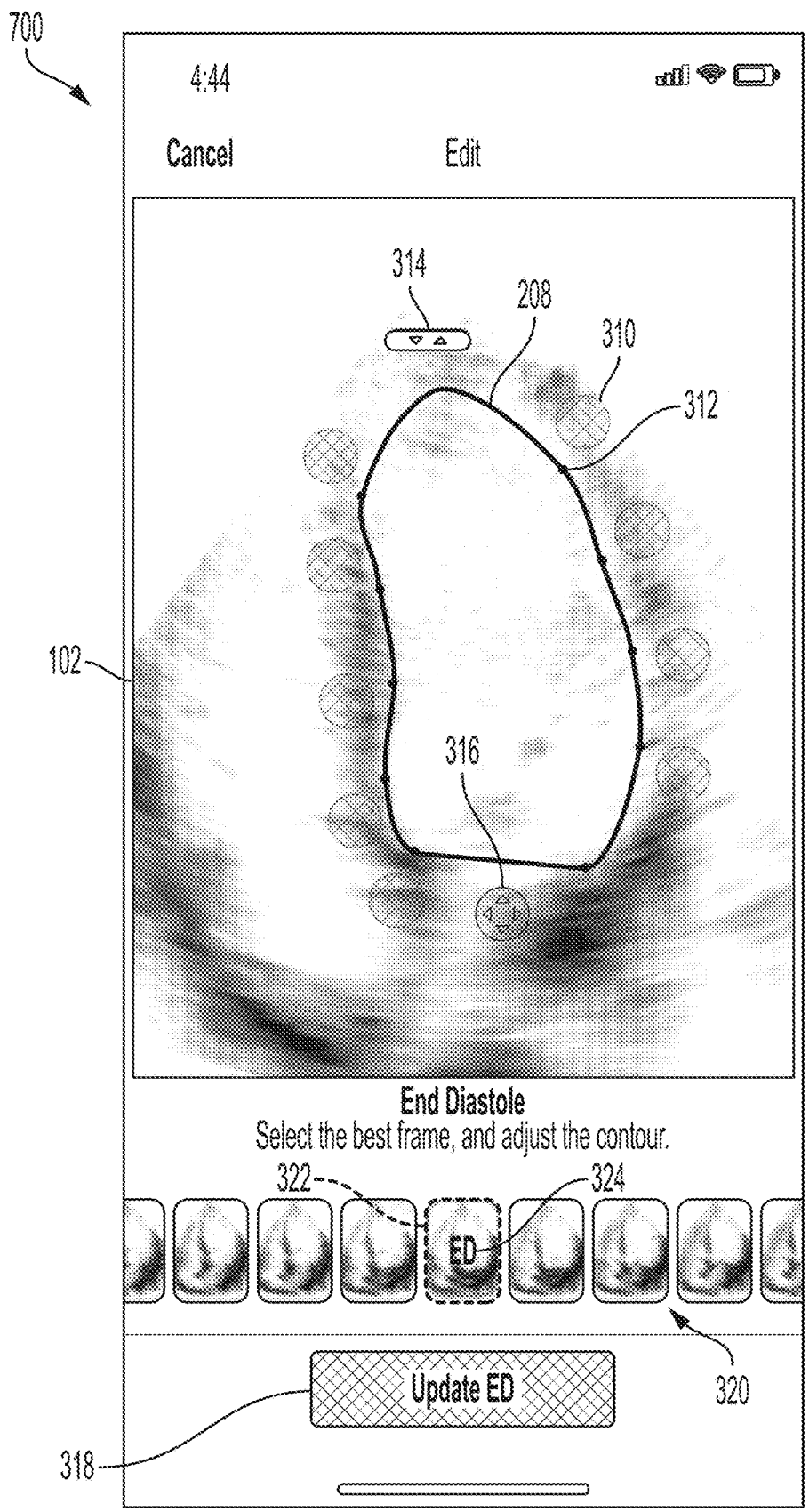
FIG. 7 illustrates an example GUI, in accordance with certain embodiments described herein.

FIG. 7 illustrates an example GUI 700, in accordance with certain embodiments described herein. The GUI 700 may be shown after selection of the first icon 314 from the GUI 300. In FIG. 7, the cursors 310, the points 312, and the second icon 316 have been faded. This may help the user to better see the ultrasound image 102 as the trace 208 is scaled and rotated based on movement of the first icon 314.

Figure 8:
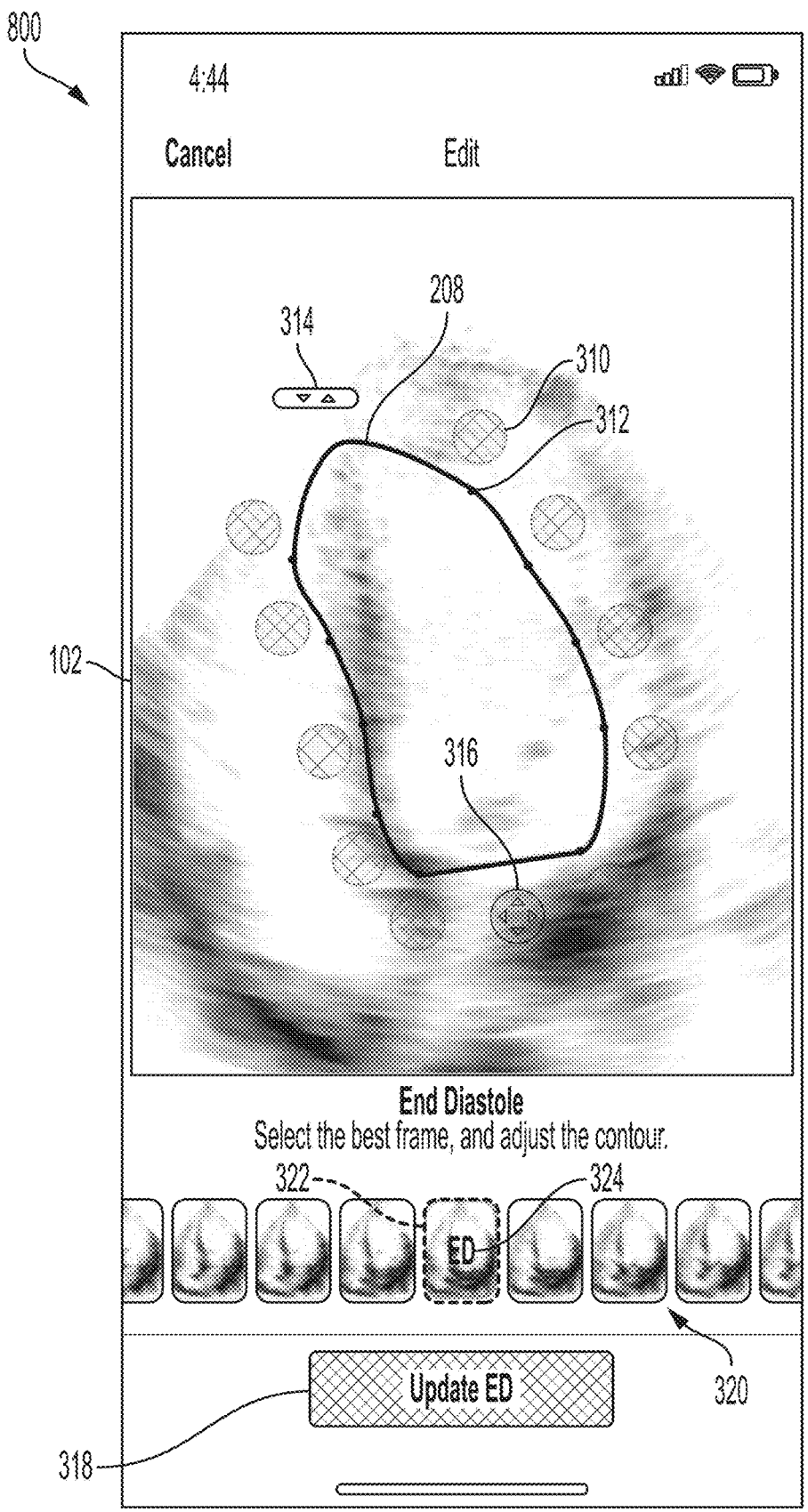
FIG. 8 illustrates an example GUI, in accordance with certain embodiments described herein.

FIG. 8 illustrates an example GUI 800, in accordance with certain embodiments described herein. The GUI 800 illustrates a rotation of the trace 208 based on and during a dragging movement beginning on or within a threshold distance of the first icon 314 in a direction perpendicular to the long axis of the trace 208. Based on the new position of the trace 208, the processing device may display the points 312, the cursors 310, the first icon 314, and the second icon 316 in new locations. The processing device may determine the new locations for the points 312 and the cursors 310 using the methods described above with reference to FIGS. 4 and 5. The processing device may position the first icon 314 adjacent to the trace 208 such that the first icon 314 is a fixed distance outside the trace 208 along a line defined by the centroid of the area within the trace 208 and the apex of the trace 208. The processing device may position the second icon 316 adjacent to the trace 208 such that the second icon 316 is a fixed distance outside the trace 208 along a line defined by the centroid of the area within the trace 208 and the midpoint of the linear base portion of the trace 208.

Figure 9:
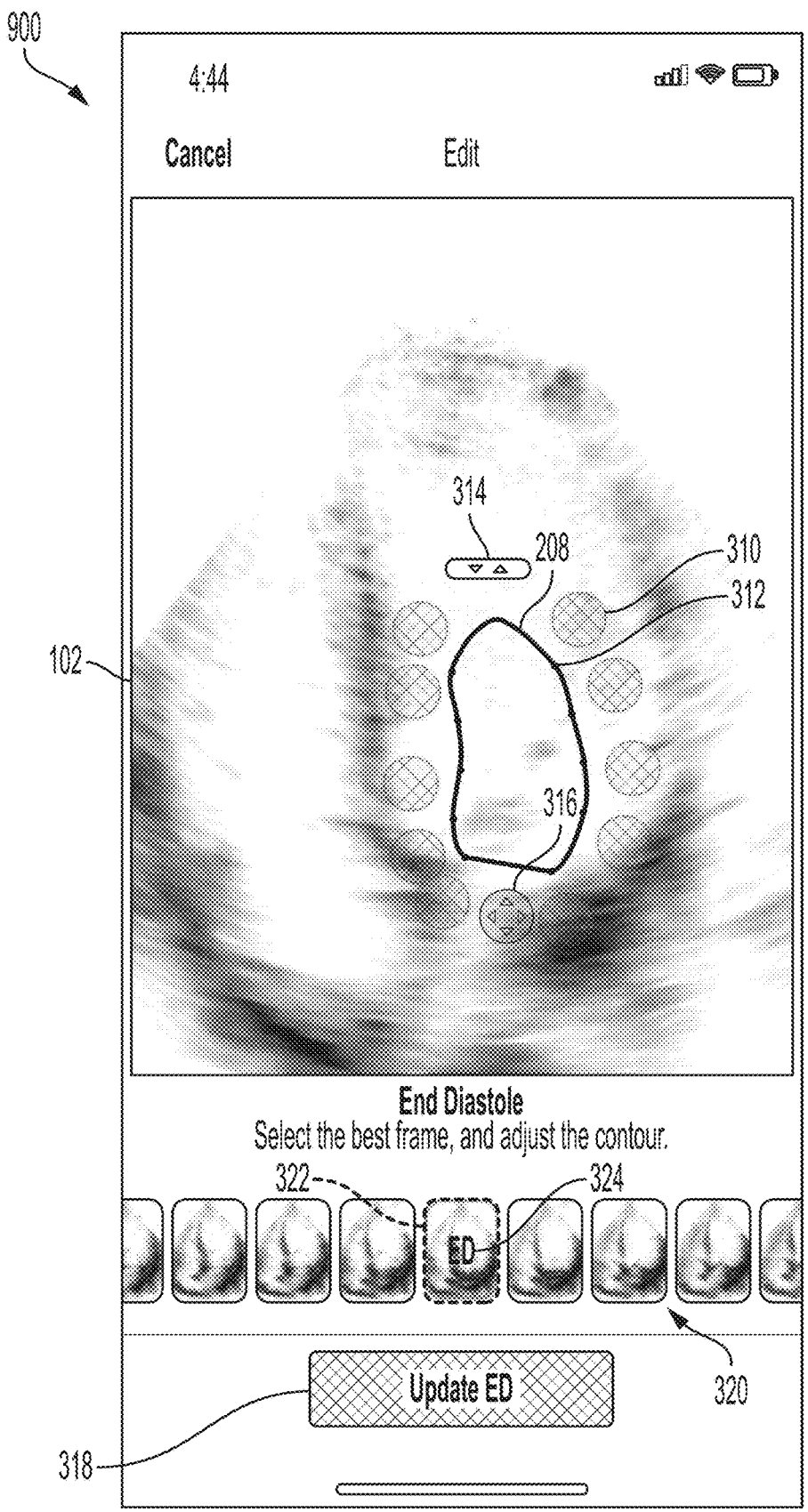
FIG. 9 illustrates an example GUI, in accordance with certain embodiments described herein.

FIG. 9 illustrates an example GUI 900, in accordance with certain embodiments described herein. The GUI 900 illustrates a scaling of the trace 208 based on and during movement of the first icon 314 in a direction along the long axis of the trace 208. Based on the new position of the trace 208, the processing device may display the points 312, the cursors 310, the first icon 314, and the second icon 316 in new locations in the manner described above.

Figure 10:
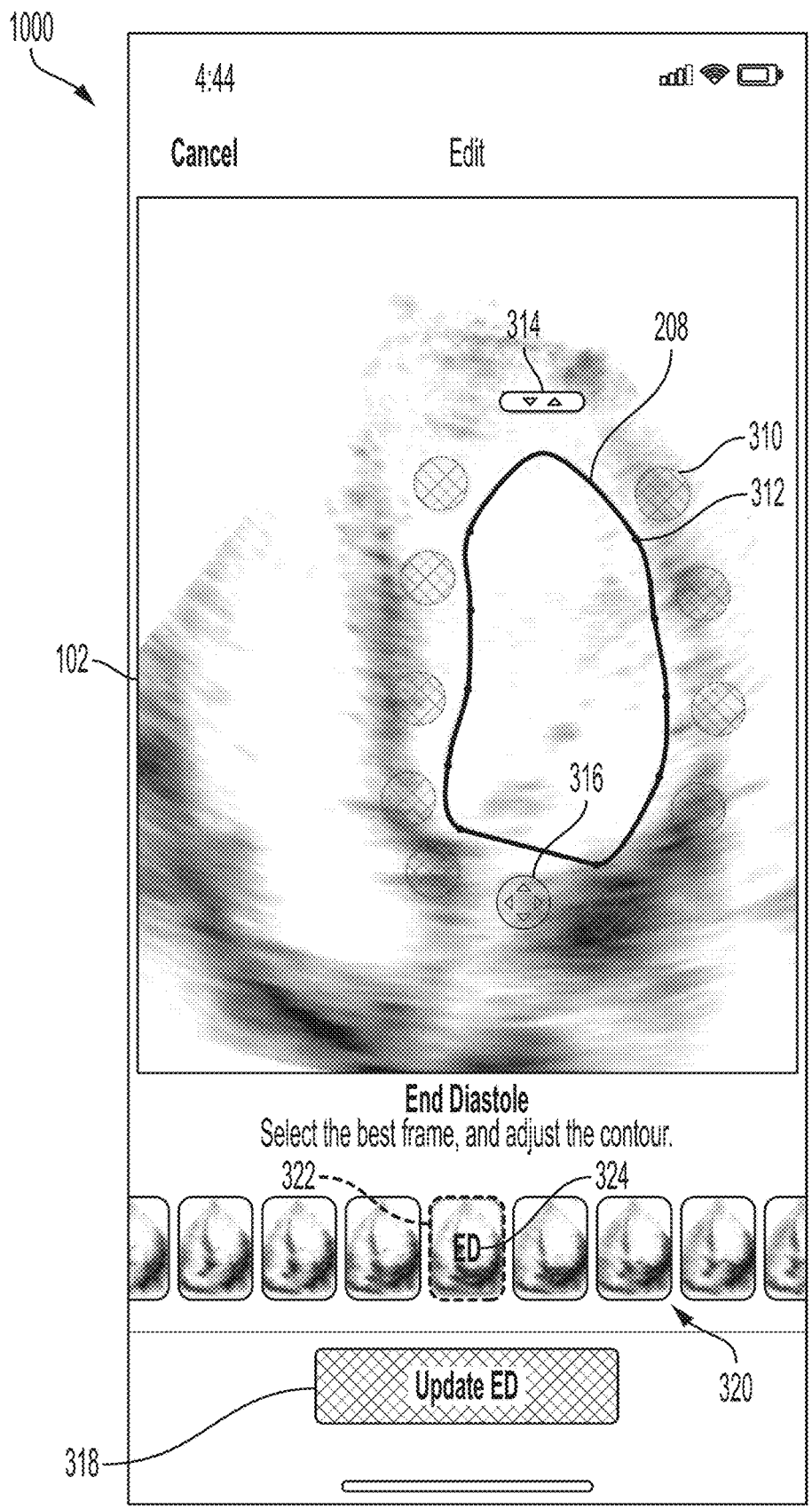
FIG. 10 illustrates an example GUI, in accordance with certain embodiments described herein.

FIG. 10 illustrates an example GUI 1000, in accordance with certain embodiments described herein. The GUI 1000 illustrates a simultaneous scaling and rotation of the trace 208 based on and during movement of the first icon 314 in an arbitrary direction. Based on the new position of the trace 208, the processing device may display the points 312, the cursors 310, the first icon 314, and the second icon 316 in new locations in the manner described above.

Figure 11:
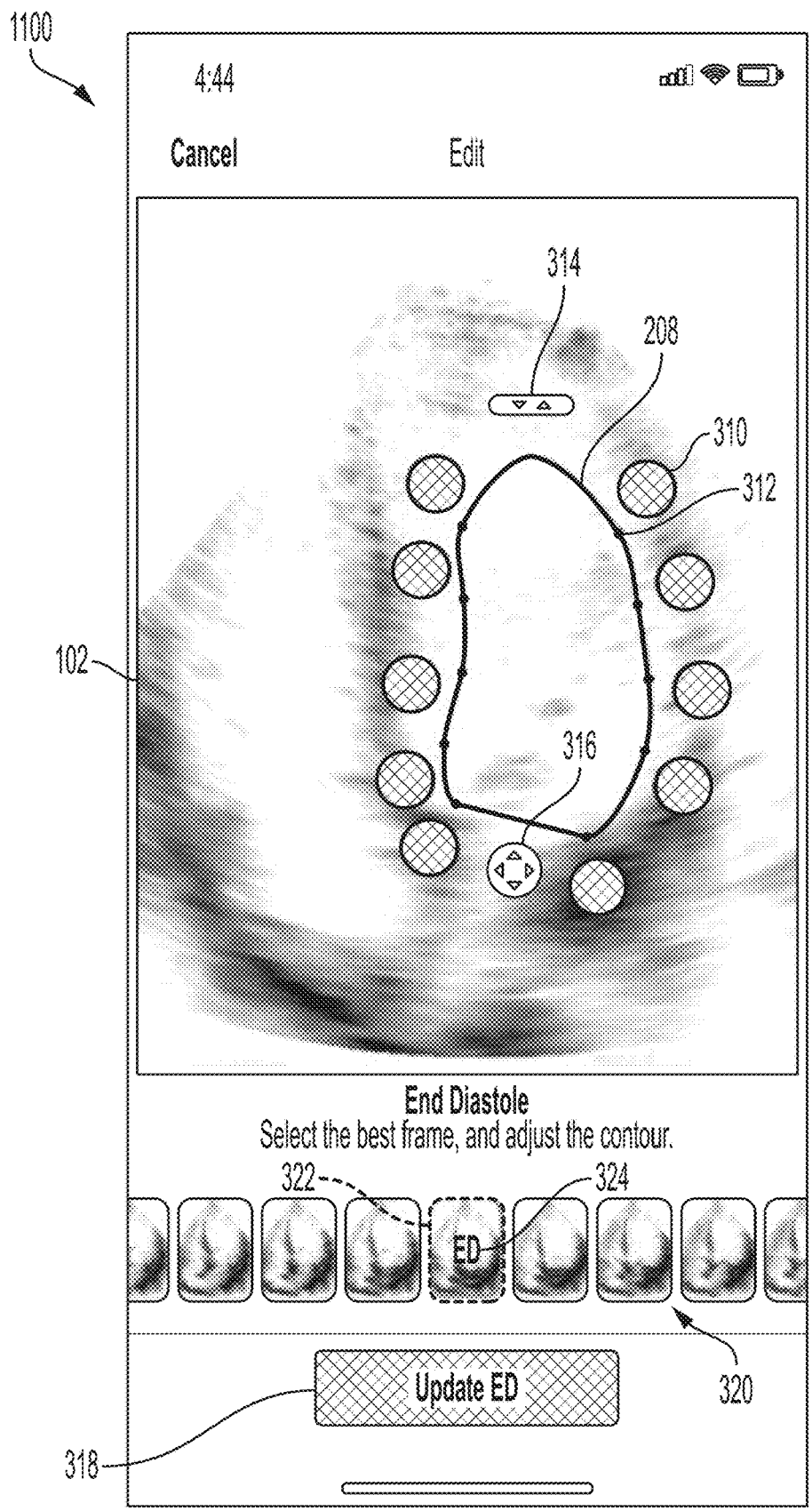
FIG. 11 illustrates an example GUI, in accordance with certain embodiments described herein.

FIG. 11 illustrates an example GUI 1100, in accordance with certain embodiments described herein. The GUI 1100 may be shown when the first icon 314 is released (e.g., by ceasing to touch a touch-sensitive display screen). The cursors 310, the points 312, and the second icon 316 are no longer faded.

Figure 12:
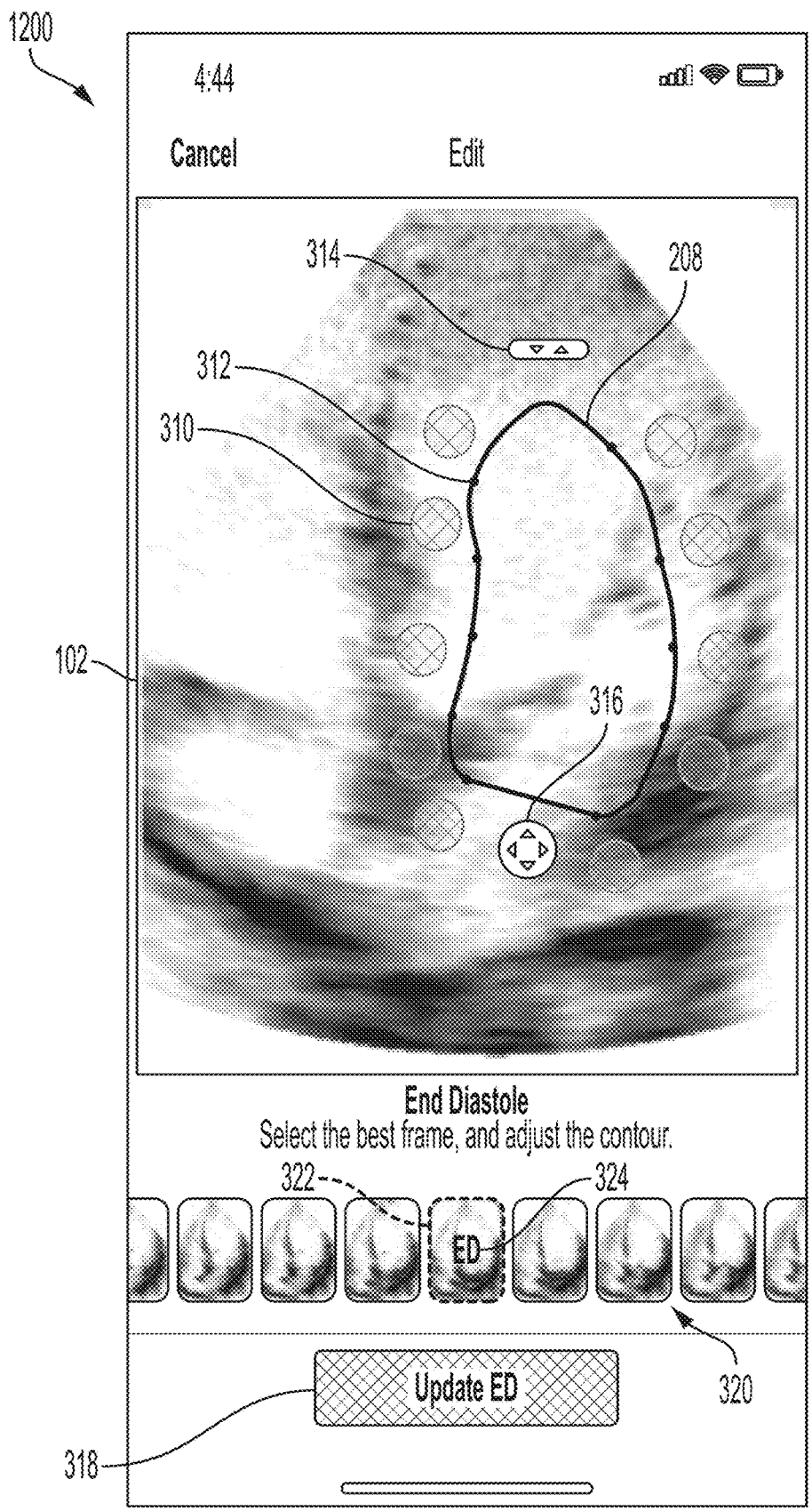
FIG. 12 illustrates an example GUI, in accordance with certain embodiments described herein.

FIG. 12 illustrates an example GUI 1200, in accordance with certain embodiments described herein. The GUI 1200 illustrates translation of the trace 208 based on and during movement of the second icon 316. In some embodiments, in response to detecting a dragging movement that begins on or within a threshold distance of the second icon 316, the processing device may translate the entire trace 208 by the distance covered by the dragging movement. For example, if the dragging movement covers x pixels in the horizontal direction and y pixels in the vertical direction, the processing device may translate the endpoints bordering the base portion of the trace 208, the apex of the trace 208, and the multiple points along the trace 208 between the apex each of the endpoints by x pixels in the horizontal direction and y pixels in the vertical direction. The processing device may then recalculate the positions of the points 312, the cursors 310, the first icon 314, and the second icon 316 based on the new location of the trace 208 in the manner described above. From when the second icon 316 is selected until it is released, the cursors 310, the points 312, and the first icon 314 may be faded.

Figure 13:
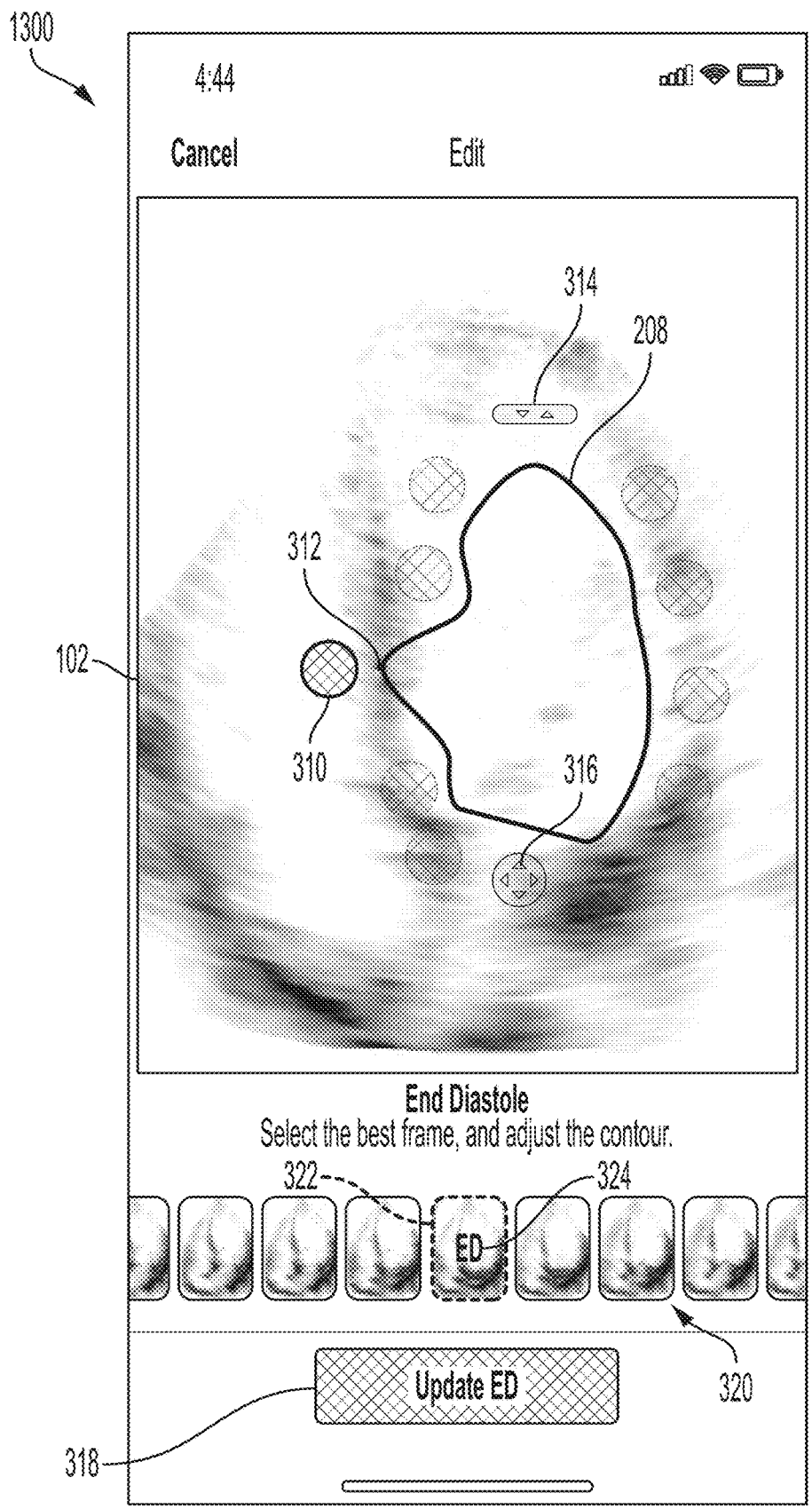
FIG. 13 illustrates an example GUI, in accordance with certain embodiments described herein.

FIG. 13 illustrates an example GUI 1300, in accordance with certain embodiments described herein. The processing device may display the GUI 1300 after detecting a dragging movement beginning on or within a threshold distance of the particular cursor labeled as 310 in FIG. 13. In some embodiments, when the processing device detects a dragging movement that begins at the cursor 310, the processing device may display the cursor 310 at a new location equivalent to the distance of the dragging movement. For example, if the processing device detects a dragging movement that begins at the cursor 310 and proceeds x pixels in the horizontal direction and y pixels in the vertical direction, the processing device may display the cursor 310 at a new location that is x pixels in the horizontal direction and y pixels in the vertical direction away from the old location of the cursor 310. The processing device may then move the point 312 corresponding to the cursor 310 to a new location that is a fixed distance away from the new location of the cursor 310 toward the centroid of the area within the trace 208, where the fixed distance is along a line from the new location of the cursor 310 to the centroid of the area within the trace 208.

For example, consider that the cursor 310 is located at (cx, cy), the corresponding point 312 is located (at px, py), the centroid of the area within the trace 208 is at (cex, cey), and a dragging movement begins at the location of the cursor 310 and covers a distance of (dx, dy). The processing device may move the cursor 310 to (cx+dx, cy+dy). The processing device may move the point 312 to a new location (px2, py2) such that the following relationships are satisfied: sqrt((cx+dx−px2)^2+(cy+dy−py2)^2)=d, where d is a fixed distance, and (cy+dy−py2)/(cx+dx−px2)=(py2−cey)/(px2−cex).

In some embodiments, as the processing device detects a dragging movement that begins at the cursor 310, the processing device may display the point 312 corresponding to the cursor 310 at a new location equivalent to the distance of the dragging movement. For example, if the processing device detects a dragging movement that begins at the cursor 310 and proceeds x pixels in the horizontal direction and y pixels in the vertical direction, the processing device may display the point 312 at a new location that is x pixels in the horizontal direction and y pixels in the vertical direction away from the old location of the point 312. The processing device may then move the cursor 310 to a new location that is a fixed distance away from the new location of the point 312 and away from the centroid of the area within the trace 208, where the fixed distance is along a line from the new location of the cursor 310 to the centroid of the area within the trace 208.

For example, consider a display screen where each location can be described with a horizontal pixel x and a vertical pixel y, or (x, y) for short. Further consider that the cursor 310 is located at (cx, cy), the corresponding point 312 is located (at px, py), the centroid of the area within the trace 208 is (cex, cey), and a dragging movement begins at the location of the cursor 310 and covers a distance of (dx, dy). The processing device may move the point 312 to (px+dx, py+dy). The processing device may move the cursor 310 to a new location (cx2, cy2) such that the following relationships are satisfied: sqrt((cx2−px−dx)^2+(cy2−py−dy)^2)=d, where d is a fixed distance, and (cy2−py−dy)/(cx2−px−dx) =(py+dy−cey)/(px+dx−cex).

Figure 14:
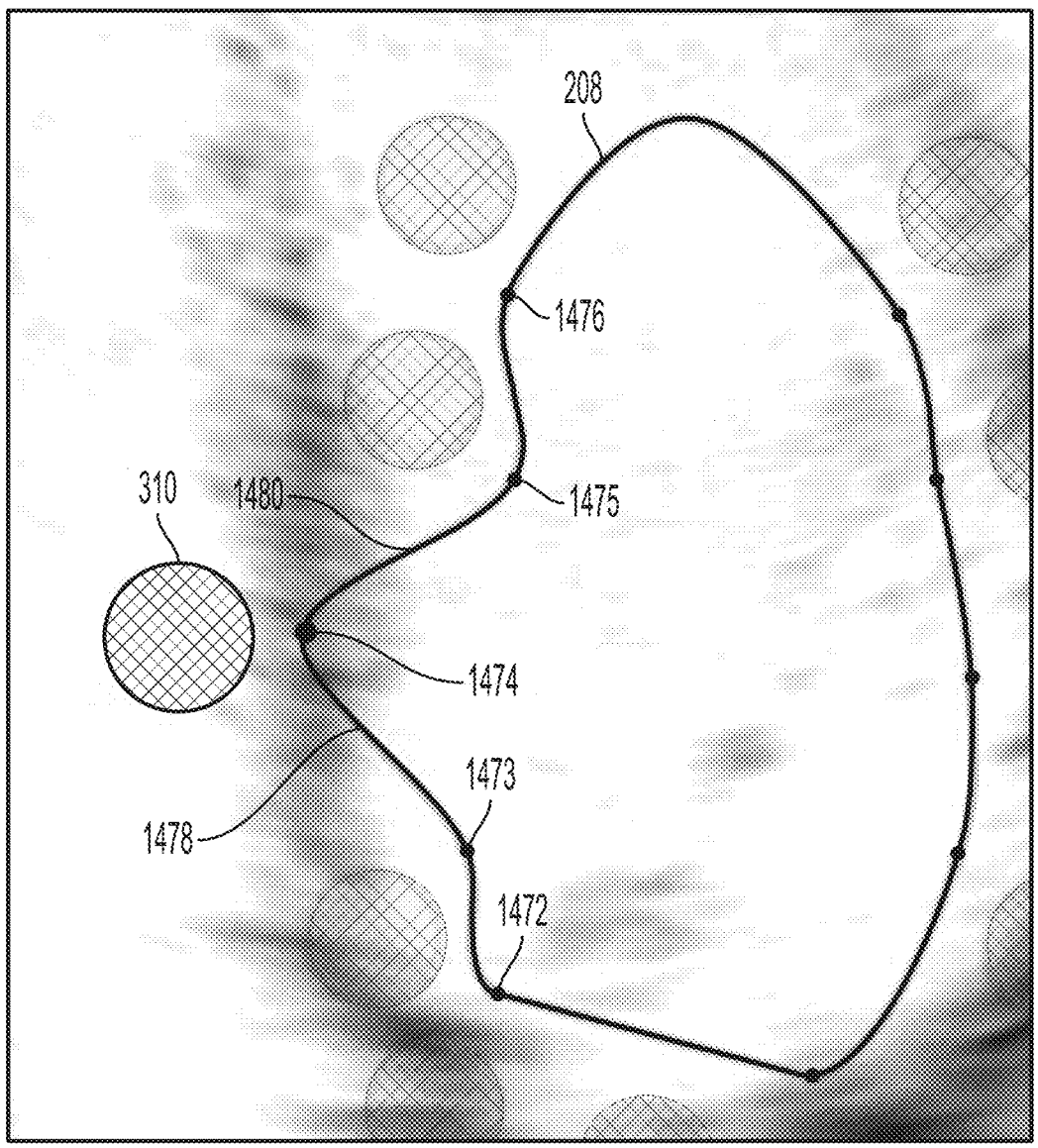
FIG. 14 illustrates a method for redrawing a trace in response to repositioning of a point on the trace, in accordance with certain embodiments described herein.

In either of the above embodiments, the processing device may redraw portions of the trace 208 based on the new location of the point 312, as will be discussed with reference to FIG. 14. FIG. 14 illustrates a method for redrawing the trace 208 in response to repositioning of one of the points 312 on the trace 208, in accordance with certain embodiments described herein. As described above, one of the points 312 may be moved based on a dragging movement that begins on a cursor 310 corresponding to the point 312. FIG. 14 shows a cursor 310 and five points 1472-1476 that are each one of the points 312 on the trace 208. Based on a dragging movement that begins on the cursor 310, the corresponding point 1474 is repositioned. The processing device redraws two portions of the trace 208, namely portion 1478 between points 1473 and 1474 and portion 1480 between points 1474 and 1475, based on the new position of the point 1474. In some embodiments, the processing device may redraw the portion 1478 of the trace 208 as a centripetal Catmull-Rom spline using the points 1472-1475 as control points, and redraw the portion 1480 of the trace as a centripetal Catmull-Rom spline using the points 1473-1476 as control points. It should be appreciated that other interpolation methods may be used for redrawing the trace 208.

Figure 15:
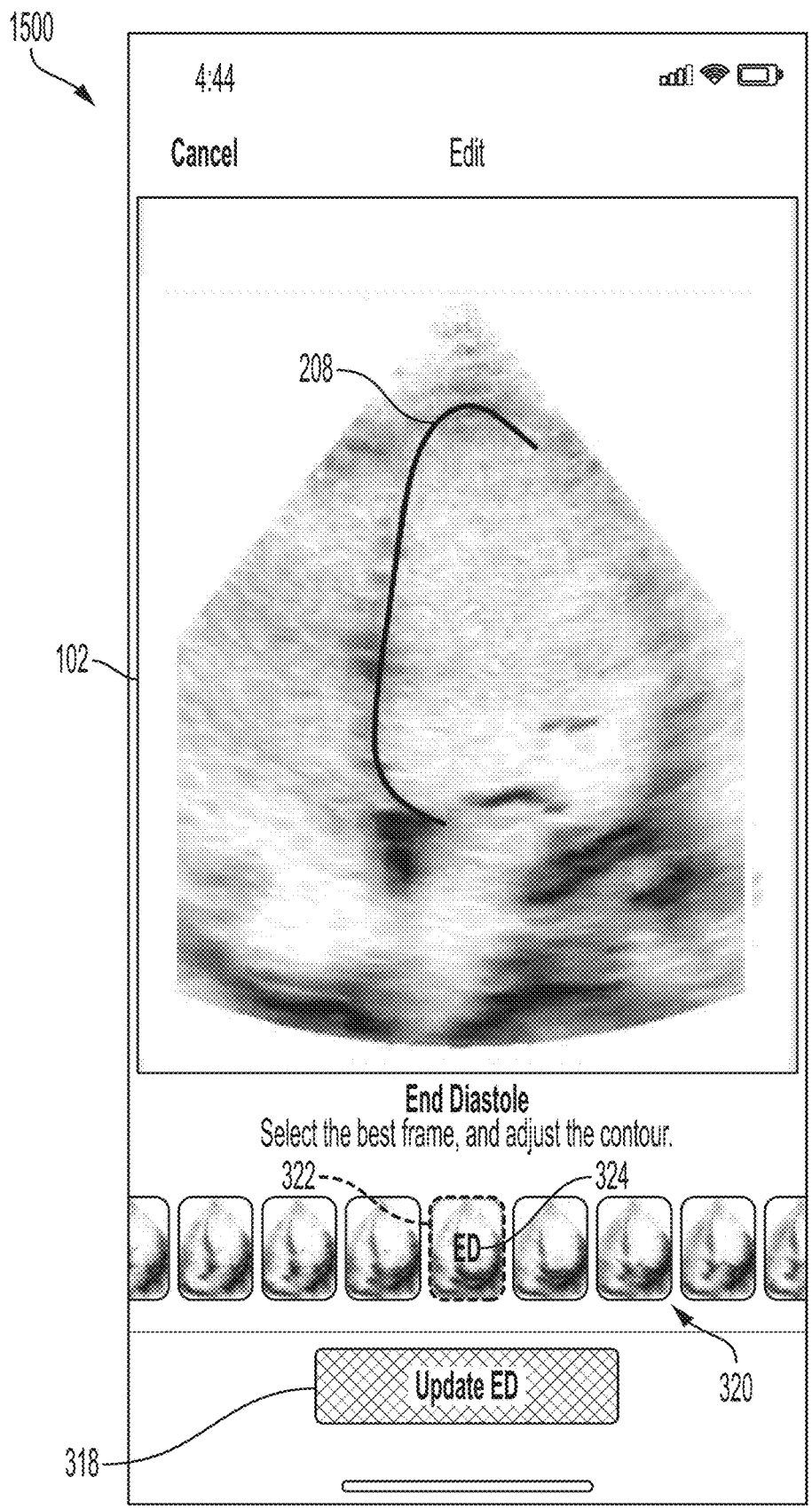
FIG. 15 illustrates an example GUI, in accordance with certain embodiments described herein.

In some embodiments, the processing device may detect a dragging movement that traces a path along a touch-sensitive display screen (e.g., the user may drag his/her finger along a path on the touch-sensitive display screen), and the processing device may display a trace along that path. Thus, rather than receiving modifications of a trace generated by a statistical model, the processing device may receive the trace from the user from scratch. In some embodiments, the processing device may not display a trace generated by a statistical model after receiving a selection of the edit option 236. In some embodiments, the processing device may display an option to modify a trace generated by a statistical model and an option to draw a new trace, and the user may select one of these options. In some embodiments, once the path traced by the dragging movement has reached the starting point of the path, the processing device may display points, cursors, the first icon, and the second icon in the manner of FIG. 3, and the user may modify the trace in the manner described above. FIG. 15 illustrates an example GUI 1500, in accordance with certain embodiments described herein. The GUI 1500 includes a trace 208 during a dragging movement that traces the trace 208.

Figure 16:
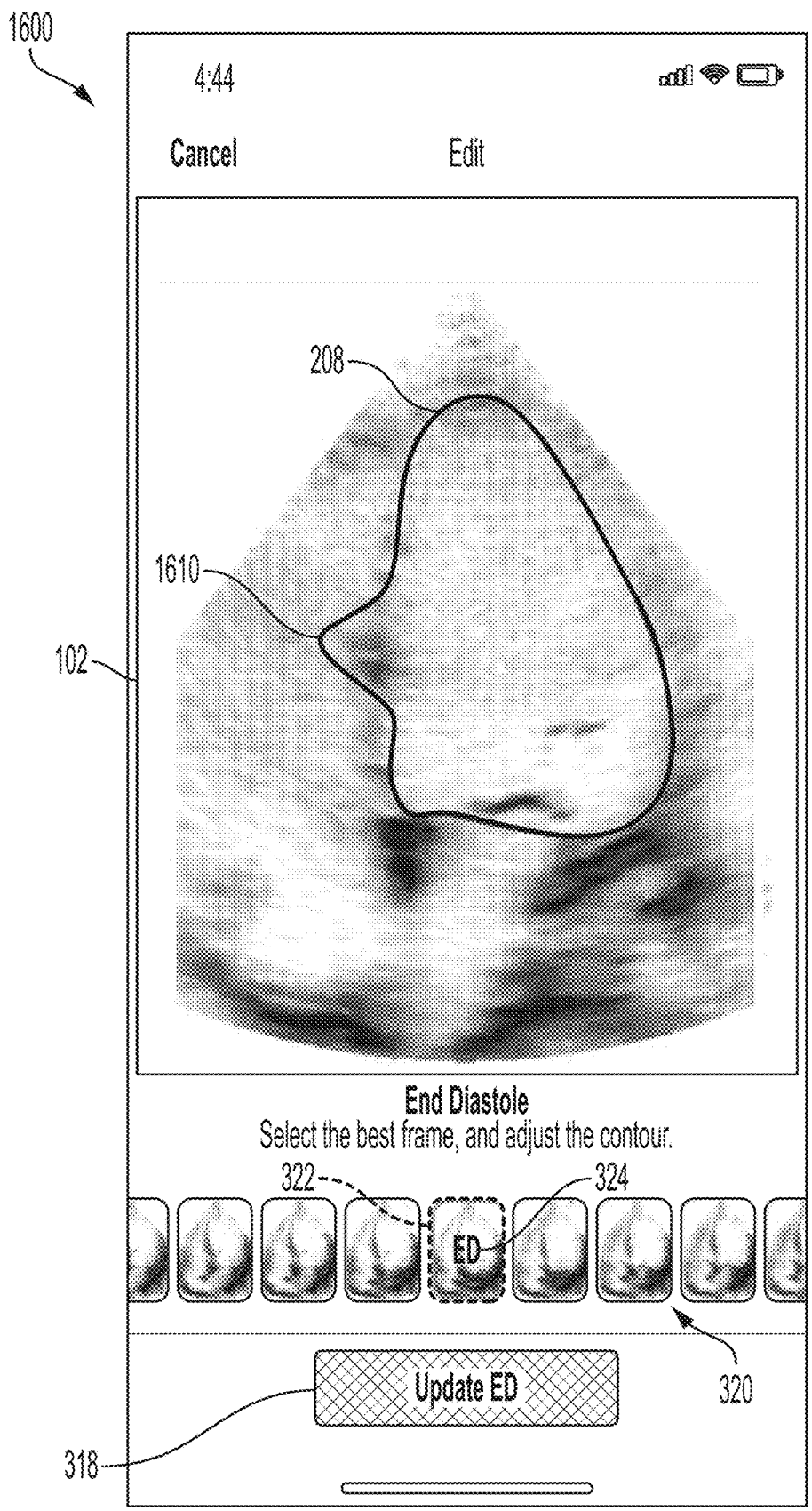
FIG. 16 illustrates an example GUI, in accordance with certain embodiments described herein.

In some embodiments, the processing device may detect a dragging movement beginning on an arbitrary selected location on a trace by a statistical model, and the processing device may modify the trace based on the dragging movement. The processing device may modify the trace in the same manner as described with reference to FIGS. 13-14. In some embodiments, the control points used for redrawing the trace using the Catmull-Rom spline method may be at locations along the trace at fixed distances from the selected location where the dragging movement began. In some embodiments, the control points used for redrawing the trace may be two closest points from among the points 312 that are to one side of the selected location and the two closest points from among the points 312 that are to another side of the selected location. In such embodiments, if one of the points 312 is within a threshold distance of the selected location, that point may be excluded from being on the control points. In some embodiments, the processing device may not display the cursors 312 and points 310, as the processing device may modify the trace 208 based on dragging movements beginning at any arbitrary location on the trace 208. FIG. 16 illustrates an example GUI 1600, in accordance with certain embodiments described herein. The GUI 1600 includes a trace 208 that has been modified based on a dragging movement that began at an arbitrary location along the trace 208 and ended at the location 1610. The trace 208 has been modified based on the dragging movement. It should be appreciated that the cursors 310 and the points 312 are not displayed by the GUI 1600.

Figure 17:
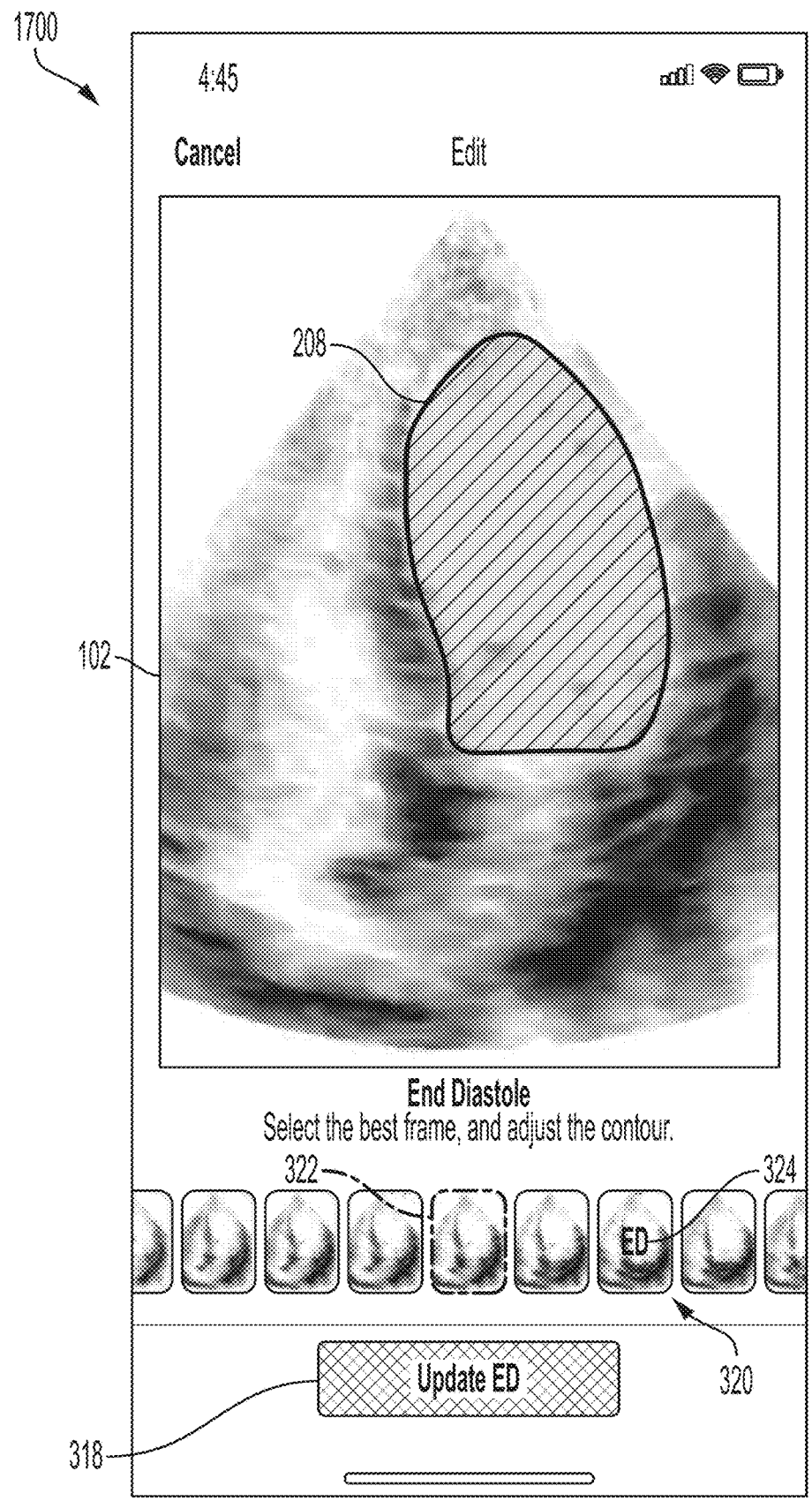
FIG. 17 illustrates an example GUI, in accordance with certain embodiment described herein.

As described above, calculation of ejection fraction may be based on volume values determined from one ultrasound image depicting a four-chamber apical view of the heart during end-diastole and another ultrasound image depicting a four-chamber apical view of the heart during end-systole. A statistical model may, initially, automatically select these two ultrasound images, but a user may modify these selections as will be described with reference to FIG. 17. FIG. 17 illustrates an example GUI 1700, in accordance with certain embodiment described herein. The processing device may display the GUI 1700 in response to the user scrolling through the ultrasound image thumbnails 320. The GUI 1700 differs from the GUI 300 in that:

1. In the GUI 1700, the current ultrasound image indicator 322 remains stationary during scrolling, but the ultrasound image thumbnails 320 move such that the current ultrasound image indicator 322 is on a different thumbnail in the ultrasound image thumbnails 320 than it was before the scrolling. The end-diastolic ultrasound image indicator 324 remains located on the same thumbnail that it was located on before the scrolling, namely the thumbnail corresponding to the image currently selected as the end-diastolic ultrasound image. Thus, the current ultrasound image indicator 322 is located on a different thumbnail than the thumbnail on which the end-diastolic ultrasound image indicator 324 is located;

2. The current ultrasound image indicator 322 has a different form (e.g., color) in the GUI 1700 than in the GUI 300, although in some embodiments the form may be the same;

3. The GUI 1700 shows an ultrasound image 102 that is different than the ultrasound image 102. In particular, the GUI 1700 shows the ultrasound image 102 corresponding to the thumbnail in the ultrasound image thumbnails 320 on which the current ultrasound image indicator 322 is located;

4. The GUI 1700 shows a trace 208 that, like the trace 208, traces the endocardial border of the left ventricle in the ultrasound image 102, but the trace 208 is filled. In some embodiments, the trace 208 may not be filled in. A statistical model may generate the trace 208; and 5. The cursors 310, the points 312, the first icon 314, and the second icon 316 are not displayed.

In response to the user ceasing to scroll through the ultrasound image thumbnails 320 such that the current ultrasound image indicator 322 is located of a particular thumbnail, the processing device may display the GUI 300, except that the GUI 300 displays the ultrasound image corresponding to the selected thumbnail, and the trace 208, cursors 310, and points 312 correspond to this ultrasound image. Referring back to FIG. 3, in response to selection of the end-diastolic ultrasound image update option 318, the processing device may:

1. Select the ultrasound image corresponding to this thumbnail as the end-diastolic ultrasound image, replacing the ultrasound image previously selected as the end-diastolic ultrasound image;
2. Move the end-diastolic ultrasound image indicator 324 to the same thumbnail as the current ultrasound image indicator 322; and
3. Display the GUI 1800.

Figure 18:
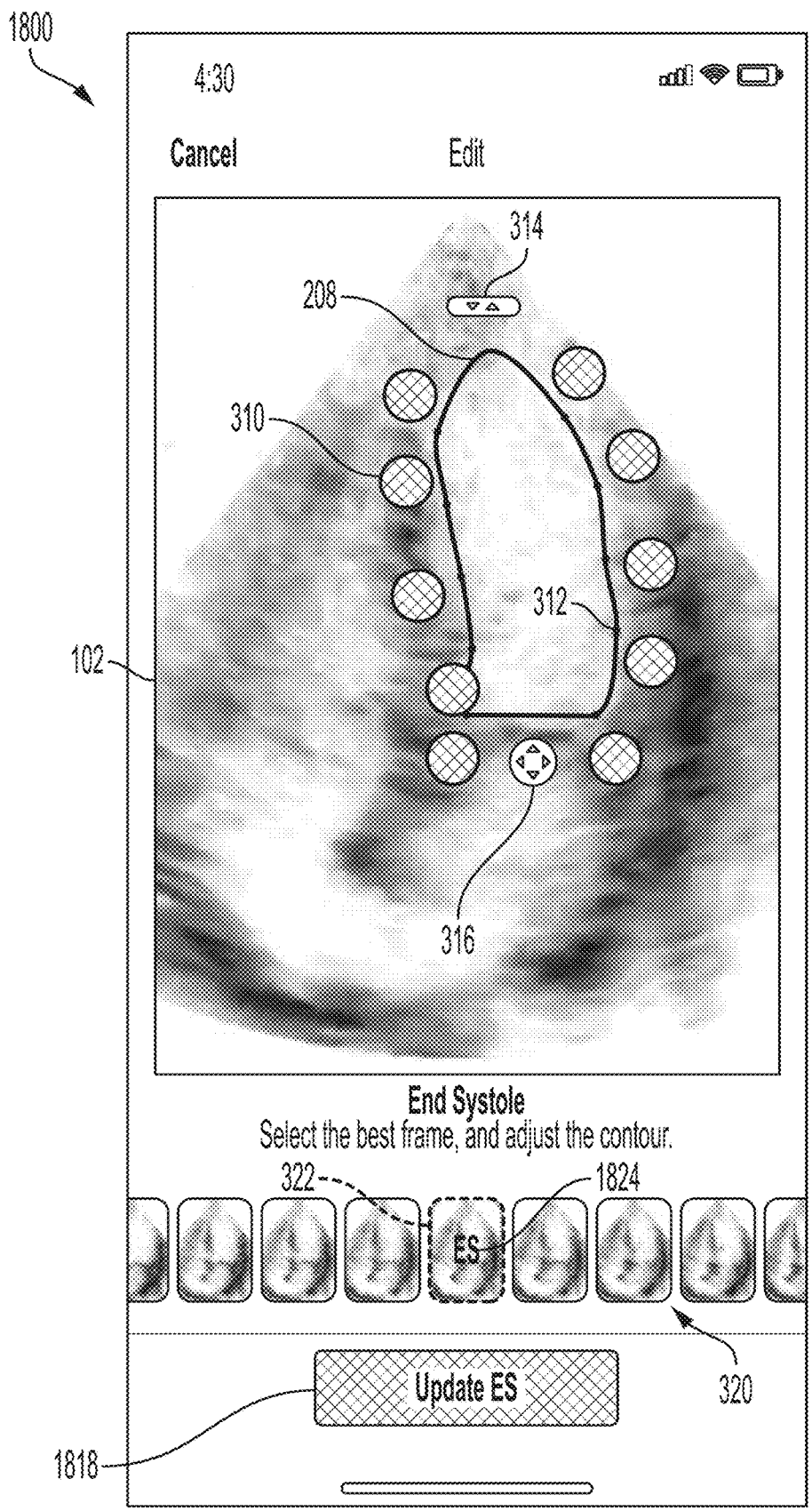
FIG. 18 illustrates an example GUI, in accordance with certain embodiments described herein.

FIG. 18 illustrates an example GUI 1800, in accordance with certain embodiments described herein. The GUI 1800 includes the ultrasound image 102, the trace 208, the cursors 1810, the points 312, the first icon 314, the second icon 316, an end-systolic ultrasound image update option 1818, the ultrasound image thumbnails 320, the current ultrasound image indicator 322, and an end-systolic ultrasound image indicator 1840. The ultrasound image 102 is the ultrasound image currently selected (either automatically by a statistical model or manually by a user) as the end-systolic ultrasound image. The trace 208, the cursors 310, and the points 312 correspond to the ultrasound image 1812. The end-systolic ultrasound image indicator 1824 is superimposed on the ultrasound image thumbnails 320 corresponding to the ultrasound image selected for end-systole. In FIG. 18, the end-systolic ultrasound image indicator 1824 includes the text "ES" (abbreviation for end-systole), although other text and/or symbols may be used. As described above, the area within the trace 208 may be used to calculate end-systolic volume ($V_{ES}$), which is used to calculate ejection fraction, by splitting the area within the trace 1808 into thin sections, assuming each sections represents a cross-section of a three-dimensional disc, and summing the disks to calculate a volume. A user may manually modify the trace 1808 in any of the manners described above for modifying the trace 208 of the ultrasound image 102. Further description of using the ultrasound image thumbnails 320 to modify selection of the end-diastolic ultrasound image may be found with reference to FIG. 19.

Figure 19:
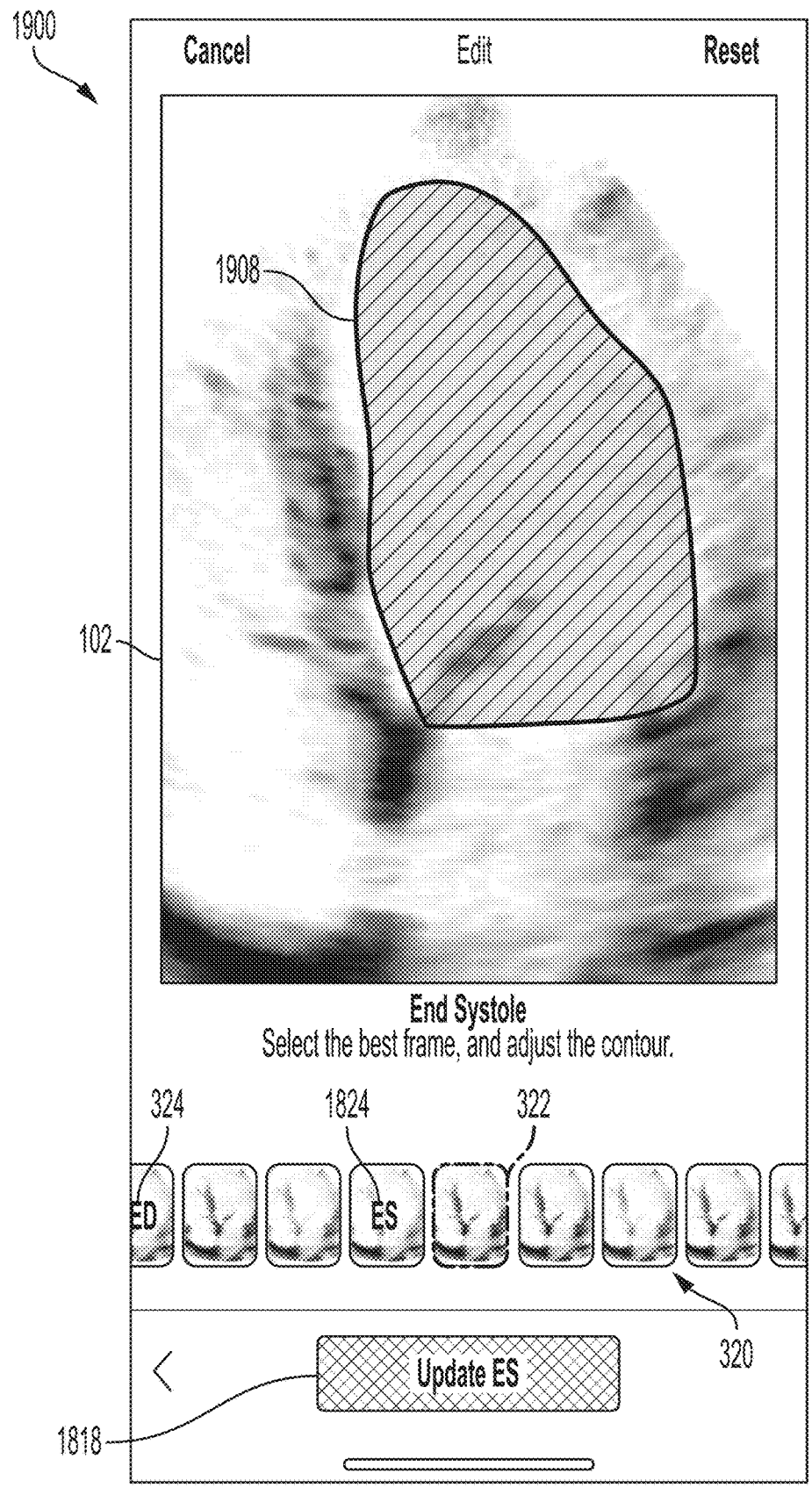
FIG. 19 illustrates an example GUI, in accordance with certain embodiments described herein.

FIG. 19 illustrates an example GUI 1900, in accordance with certain embodiments described herein. The GUI 1900 is the same as the GUI 1700, except that the end-systolic ultrasound image indicator 1824 is displayed instead of the end-diastolic ultrasound image indicator 324. In response to the user ceasing to scroll through the ultrasound image thumbnails 320 such that the current ultrasound image indicator 322 is located on a particular thumbnail, the processing device may display the GUI 1800, except that the GUI 1800 may display the ultrasound image corresponding to the selected thumbnail, and the trace 208, cursors 310, and points 312 correspond to this ultrasound image. Referring to FIG. 18, in response to selection of the end-systolic ultrasound image update option 1818, the processing device may:

1. Select the ultrasound image corresponding to this thumbnail as the end-systolic ultrasound image;
2. Move the end-systolic ultrasound image indicator 1824 on the same thumbnail as the current ultrasound image indicator 322; and
3. Display the GUI 200. When the processing device displays the GUI 200, the end-diastolic and end-systolic images and the traces on these images as displayed in the cine may be different based on the user modifications. Additionally, the automatic calculation value 206 may show a different ejection fraction value due to the user's manual modifications. Also, the GUI may include text indicating the calculation was manual, not automatic, based on the user's input.

Referring back to FIG. 1, in some embodiments, upon receiving a selection from a user of the automatic calculation option 128, the processing device may record a series of ultrasound images to a buffer. If the quality of the series of ultrasound images for performing the automatic calculation does not exceed the threshold, the processing device may not automatically select an end-diastolic ultrasound image or an end-systolic ultrasound image or automatically calculate an ejection fraction value. Instead, the processing device may display the GUI 2000, which may begin a workflow from which the user may manually select an end-diastolic ultrasound image and an end-systolic ultrasound image and manually modify traces on these ultrasound images. Thus, the user may understand that the calculation is manual and not automatic, as the statistical model may not have confidence in its ability to automatically calculate ejection fraction based on the collected ultrasound images.

Figure 20:
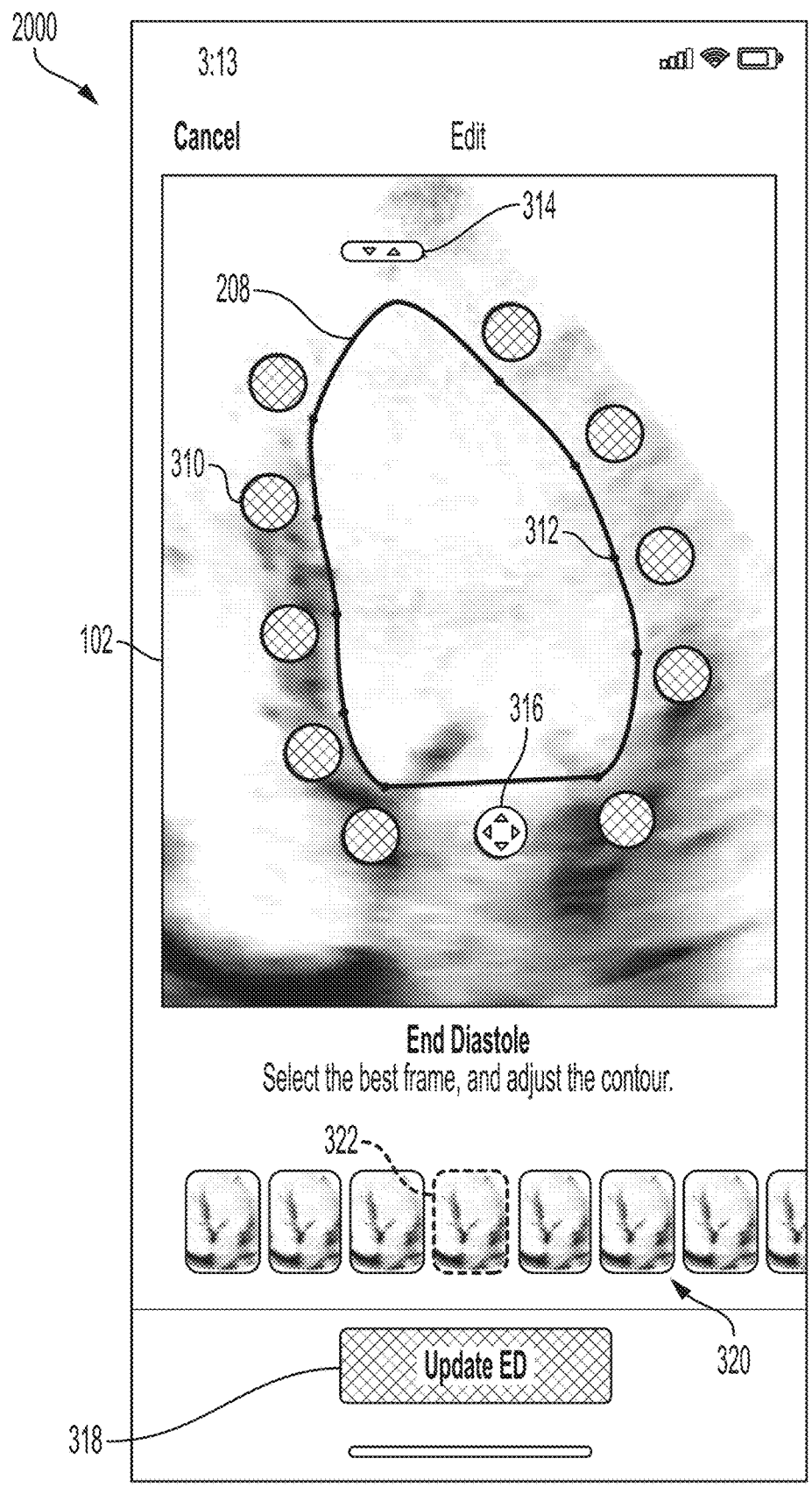
FIG. 20 illustrates an example GUI, in accordance with certain embodiments described herein.

FIG. 20 illustrates an example GUI 2000, in accordance with certain embodiments described herein. The GUI 2000 is the same as the GUI 300, except that the end-diastolic ultrasound image indicator 324 is not displayed because an end-diastolic ultrasound image has not been automatically selected. Further description of using the ultrasound image thumbnails 320 to manually select the end-diastolic ultrasound image may be found with reference to FIG. 21.

Figure 21:
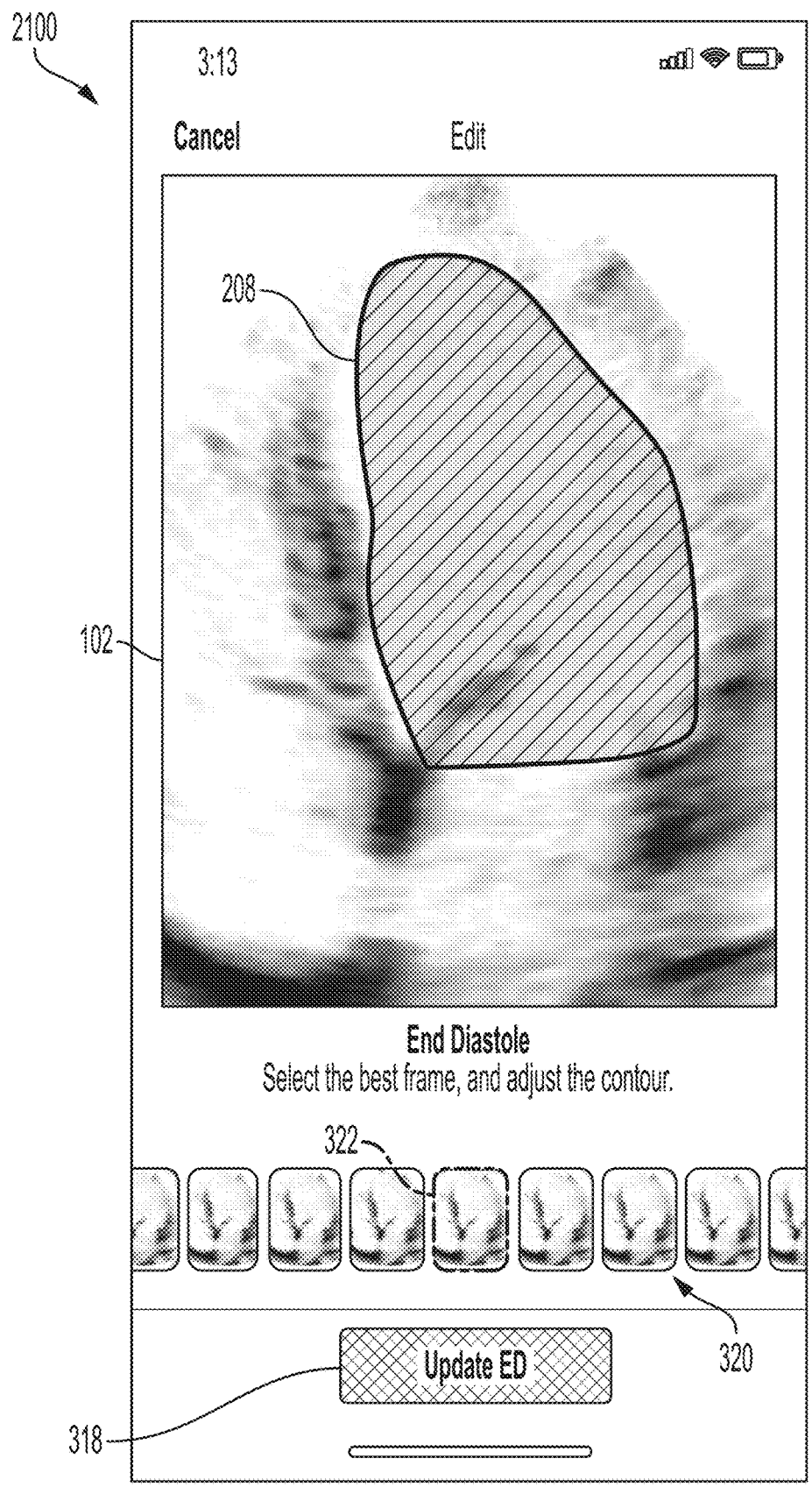
FIG. 21 illustrates an example GUI, in accordance with certain embodiments described herein.

FIG. 21 illustrates an example GUI 2100, in accordance with certain embodiments described herein. The GUI 2100 is the same as the GUI 1700, except that the end-diastolic ultrasound image indicator 324 is not displayed because an end-diastolic ultrasound image has not been automatically selected. In response to the user ceasing to scroll through the ultrasound image thumbnails 320 such that the current ultrasound image indicator 322 is located of a particular thumbnail, the processing device may display the GUI 2000, except that the GUI 2000 displays the ultrasound image corresponding to the selected thumbnail, and the trace 208, cursors 310, and points 312 correspond to this ultrasound image. Referring to FIG. 20, in response to selection of the end-diastolic ultrasound image update option 318, the processing device may:

1. Select the ultrasound image corresponding to this thumbnail as the end-diastolic ultrasound image;
2. Display the end-diastolic ultrasound image indicator 324 on the same thumbnail as the current ultrasound image indicator 322; and
3. Display the GUI 2200.

Figure 22:
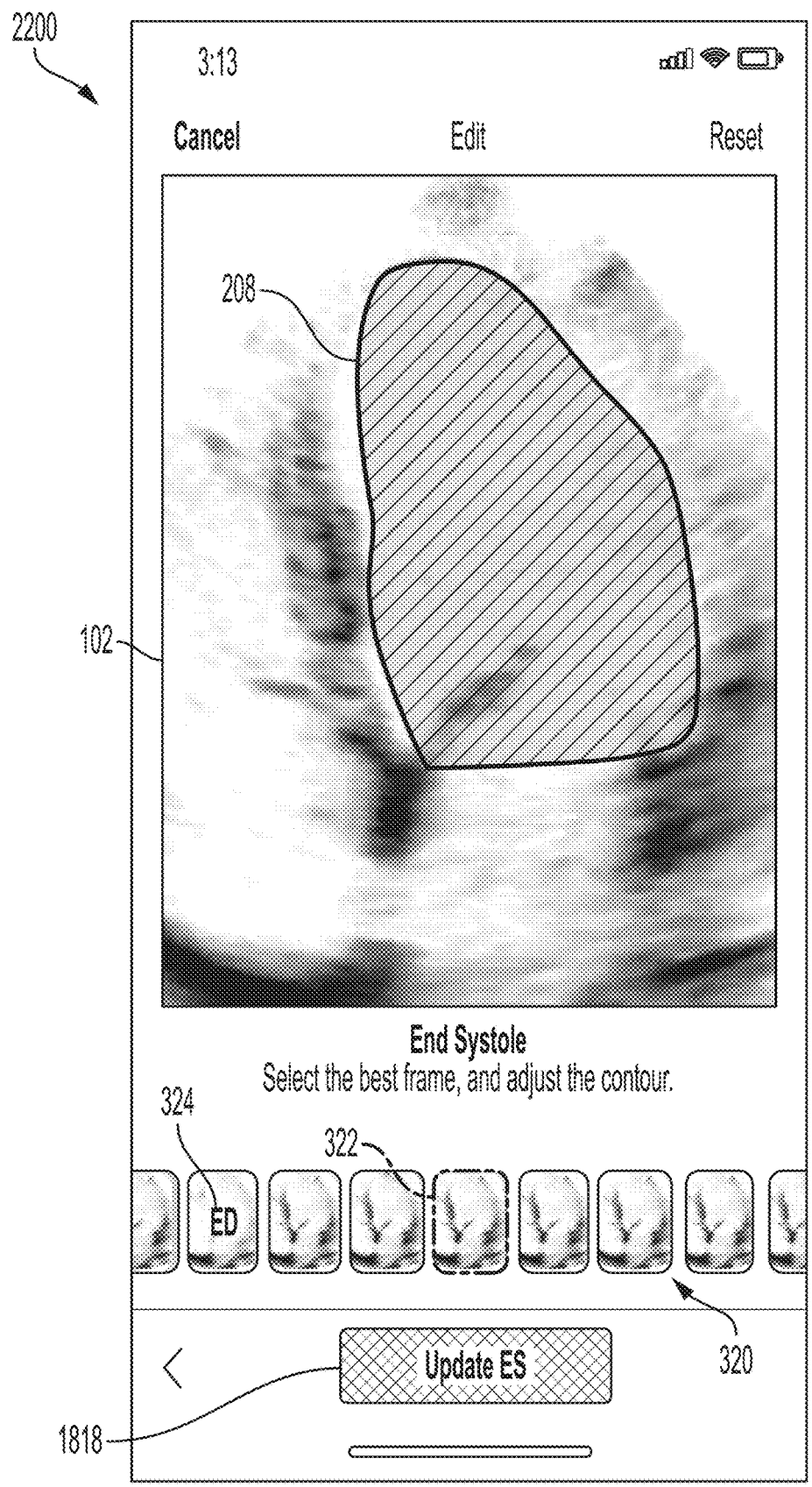
FIG. 22 illustrates an example GUI, in accordance with certain embodiments described herein.

FIG. 22 illustrates an example GUI 2200, in accordance with certain embodiments described herein. The GUI 2200 is the same as the GUI 1900, except that the end-systolic ultrasound image indicator 1824 is not displayed because an end-diastolic ultrasound image has not been automatically selected. In response to the user ceasing to scroll through the ultrasound image thumbnails 320 such that the current ultrasound image indicator 322 is located of a particular thumbnail, the processing device may display the GUI 2300.

Figure 23:
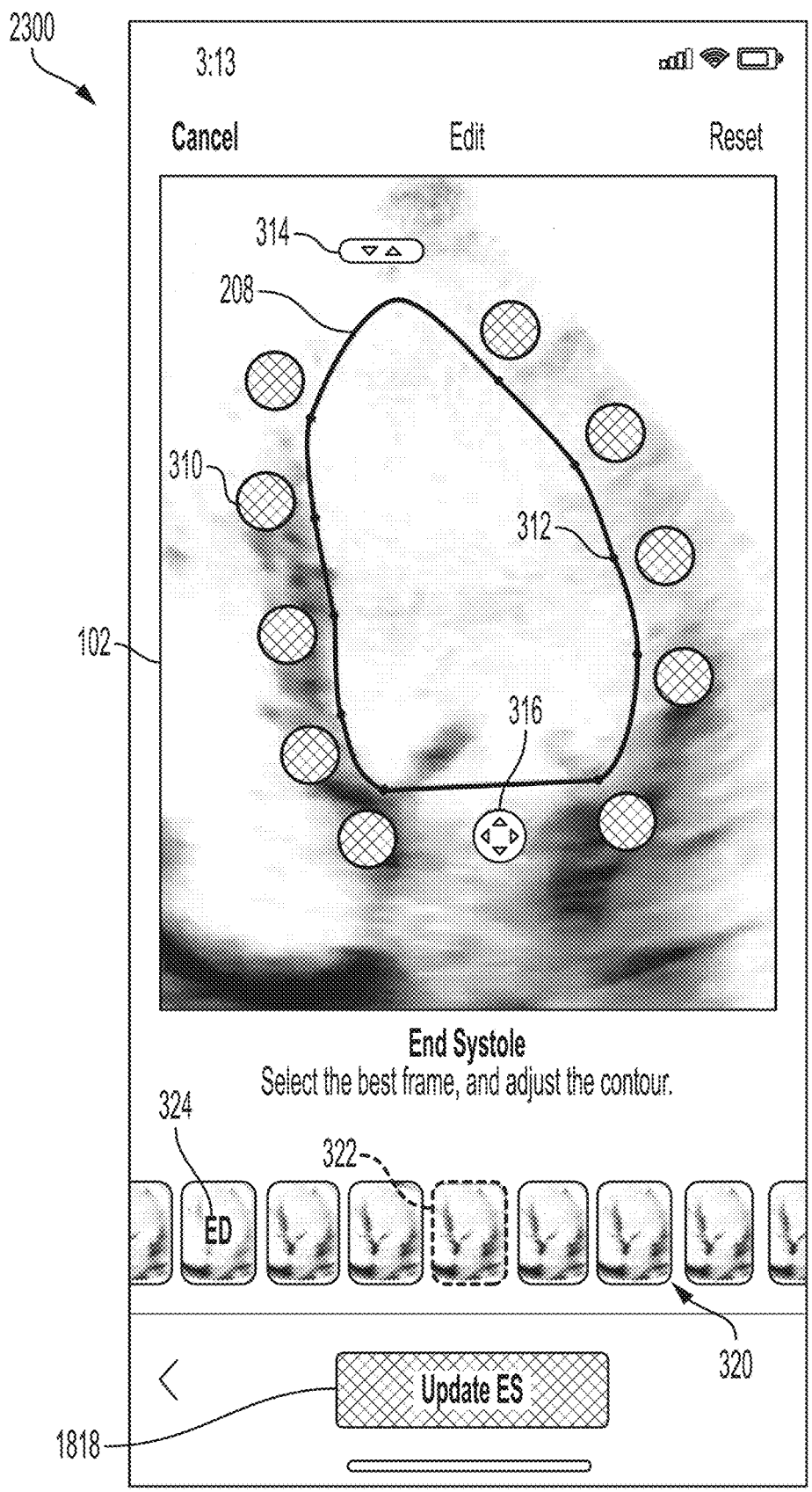
FIG. 23 illustrates an example GUI, in accordance with certain embodiments described herein.

FIG. 23 illustrates an example GUI 2300, in accordance with certain embodiments described herein. The GUI 2300 is the same as the GUI 1800, except that the end-systolic ultrasound image indicator 1824 is not displayed because an end-systolic ultrasound image has not been automatically selected. Further description of using the ultrasound image thumbnails 320 to manually select the end-systolic ultrasound image may be found with reference to FIG. 22. In response to selection of the end-systolic ultrasound image update option 1818, the processing device may:

1. Select the ultrasound image corresponding to this thumbnail as the end-systolic ultrasound image;
2. Display the end-systolic ultrasound image indicator 1824 on the same thumbnail as the current ultrasound image indicator 322; and
3. Display the GUI 200.

It should be appreciated that the cursors 310, the points 312, the first icon 314, and the second icon 316 may have different forms or locations than those shown in the figures. Also, the GUI may include text indicating the calculation was manual, not automatic, based on the user's input.

While the above description has described GUIs for modifying selection of the end-diastolic and end-systolic ultrasound images and for modifying traces on ultrasound images to calculate ejection fraction, it should be understood that the GUIs may also be used for selecting ultrasound images from a series and modifying traces on ultrasound images for other types of calculations.

Figure 24:
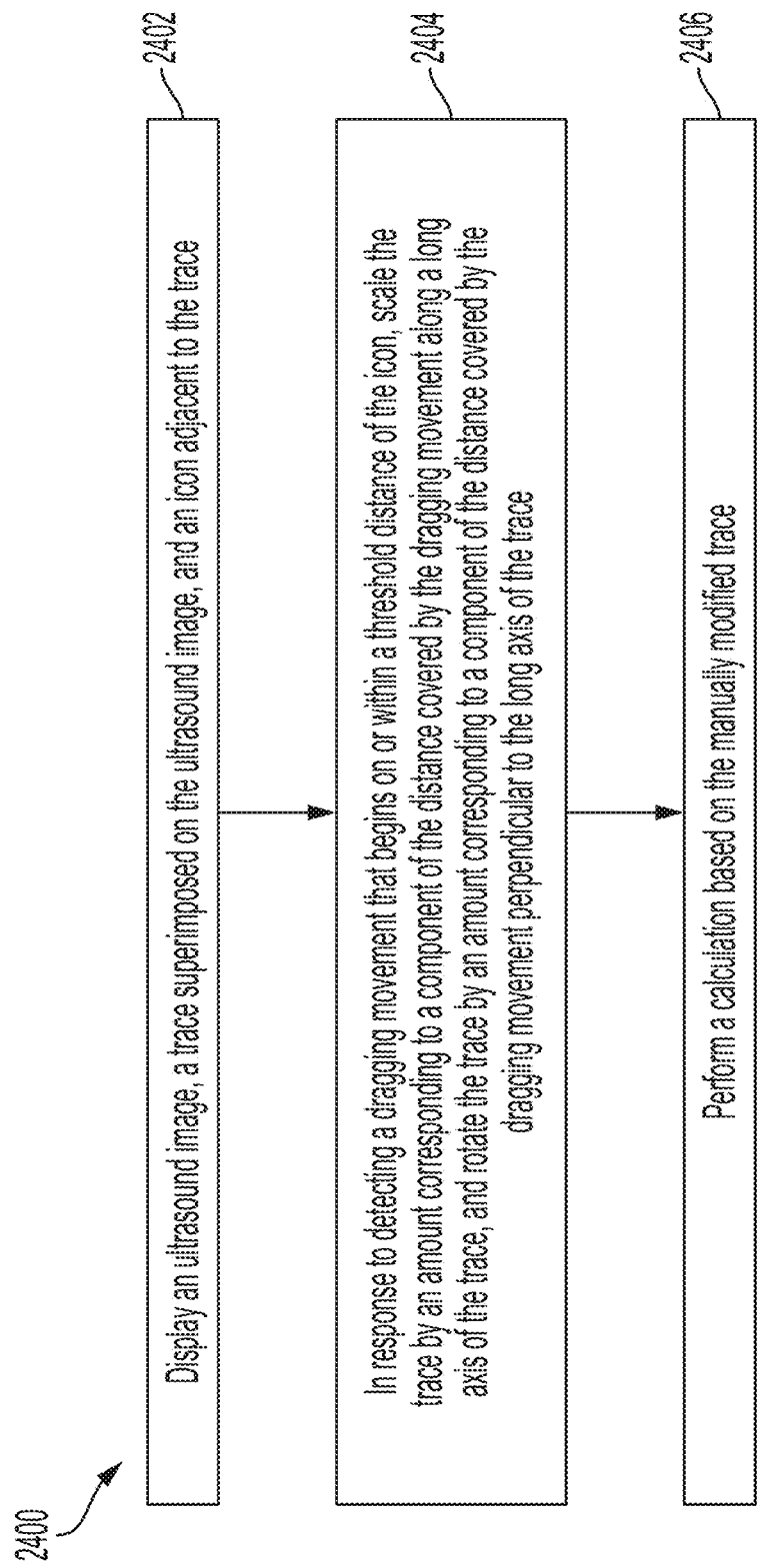
FIG. 24 illustrates an example process for enabling a user to manually modify an input to a calculation performed based at least in part on an ultrasound image, in accordance with certain embodiments described herein.

FIG. 24 illustrates an example process 2400 for enabling a user to manually modify an input to a calculation performed based at least in part on an ultrasound image, in accordance with certain embodiments described herein. The process 2400 is performed by a processing device in operative communication with an ultrasound device.

In act 2402, the processing device displays an ultrasound image (e.g., the ultrasound image 102), a trace (e.g., the trace 208) superimposed on the ultrasound image, and an icon (e.g., the first icon 314) adjacent to the trace. Further description of act 2402 may be found with reference to FIG. 3. The process 2400 proceeds from act 2402 to act 2404.

In act 2404, in response to detecting a dragging movement that begins on or within a threshold distance of the icon, the processing device scales the trace by an amount corresponding to a component of the distance covered by the dragging movement along a long axis of the trace, and rotates the trace by an amount corresponding to a component of the of the distance covered by the dragging movement perpendicular to the long axis of the trace. Further description of act 2404 may be found with reference to FIGS. 6-10. The process 2400 proceeds from act 2404 to act 2406.

In act 2406, the processing device performs a calculation (e.g., calculation of ejection fraction) based on the manually modified trace (e.g., based on the area within the trace). Further description of act 2406 may be found with reference to FIG. 2.

Figure 25:
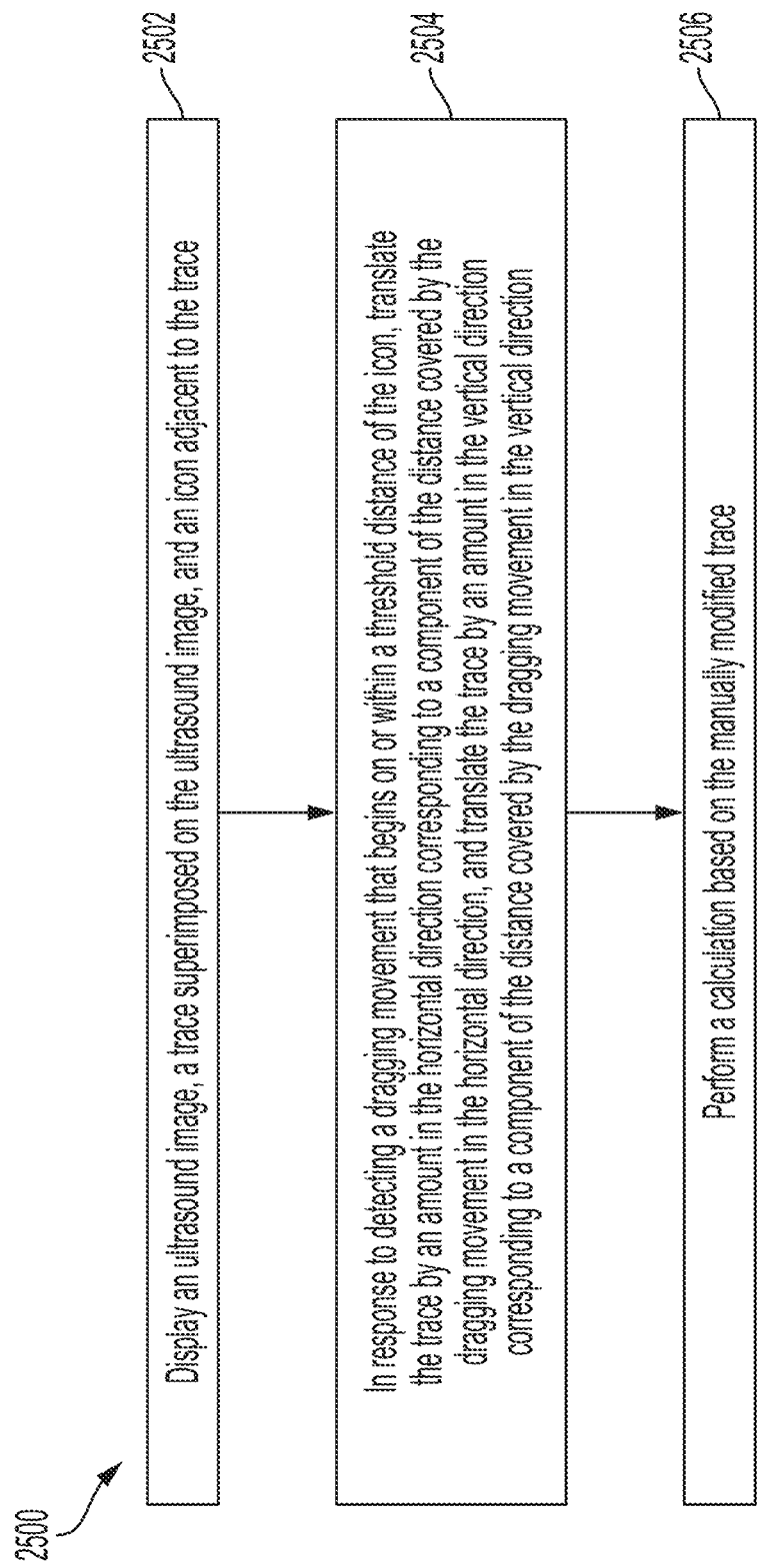
FIG. 25 illustrates an example process for enabling a user to manually modify an input to a calculation performed based at least in part on an ultrasound image, in accordance with certain embodiments described herein.

FIG. 25 illustrates an example process 2500 for enabling a user to manually modify an input to a calculation performed based at least in part on an ultrasound image, in accordance with certain embodiments described herein. The process 2500 is performed by a processing device in operative communication with an ultrasound device.

In act 2502, the processing device displays an ultrasound image (e.g., the ultrasound image 102), a trace (e.g., the trace 208) superimposed on the ultrasound image, and an icon (e.g., the second icon 316) adjacent to the trace. Further description of act 2502 may be found with reference to FIG. 3. The process 2500 proceeds from act 2502 to act 2504.

In act 2504, in response to detecting a dragging movement that begins on or within a threshold distance of the icon, the processing device translates the trace by an amount in the horizontal direction corresponding to a component of the distance covered by the dragging movement in the horizontal direction, and translates the trace by an amount in the vertical direction corresponding to a component of the distance covered by the dragging movement in the vertical direction. Further description of act 2504 may be found with reference to FIG. 12. The process 2500 proceeds from act 2504 to act 2506.

In act 2506, the processing device performs a calculation (e.g., calculation of ejection fraction) based on the manually modified trace (e.g., based on the area within the trace). Further description of act 2506 may be found with reference to FIG. 2.

Figure 26:
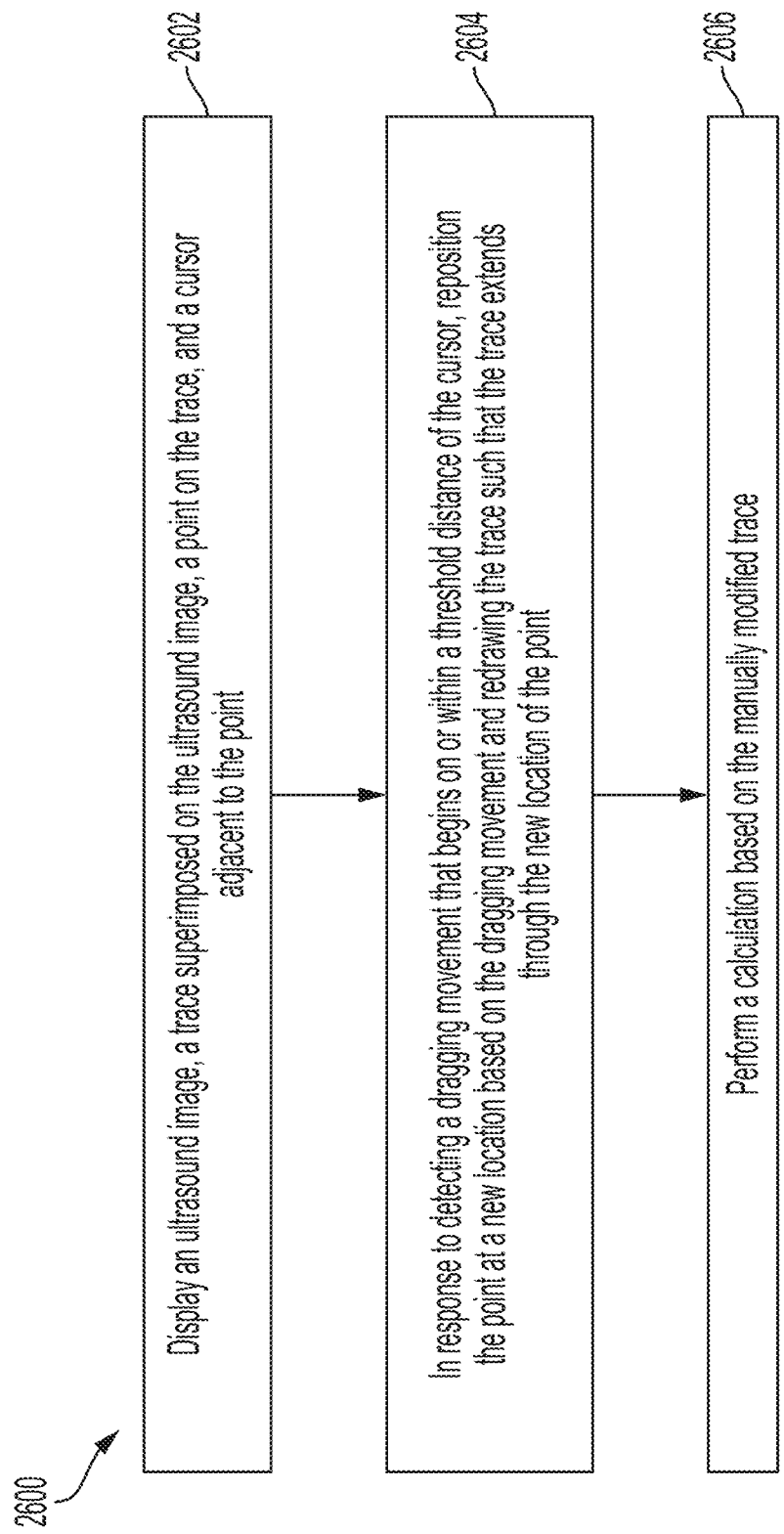
FIG. 26 illustrates an example process for enabling a user to manually modify an input to a calculation performed based at least in part on an ultrasound image, in accordance with certain embodiments herein.

FIG. 26 illustrates an example process 2600 for enabling a user to manually modify an input to a calculation performed based at least in part on an ultrasound image, in accordance with certain embodiments described herein. The process 2600 is performed by a processing device in operative communication with an ultrasound device.

In act 2602, the processing device displays an ultrasound image (e.g., the ultrasound image 102), a trace (e.g., the trace 208) superimposed on the ultrasound image, a point (e.g., a point 312) on the trace, and a cursor (e.g., a cursor 310) adjacent to the point. Further description of act 2602 may be found with reference to FIG. 3. The process 2600 proceeds from act 2602 to act 2604.

In act 2604, in response to detecting a dragging movement that begins on or within a threshold distance of the cursor, the processing device repositions the point at a new location based on the dragging movement and redraws the trace such that the trace extends through the new location of the point. Further description of act 2604 may be found with reference to FIGS. 13-14. The process 2600 proceeds from act 2604 to act 2606.

In act 2606, the processing device performs an automatic calculation (e.g., calculation of ejection fraction) based on the manually modified trace (e.g., based on the area within the trace). Further description of act 2606 may be found with reference to FIG. 2.

Figure 27:
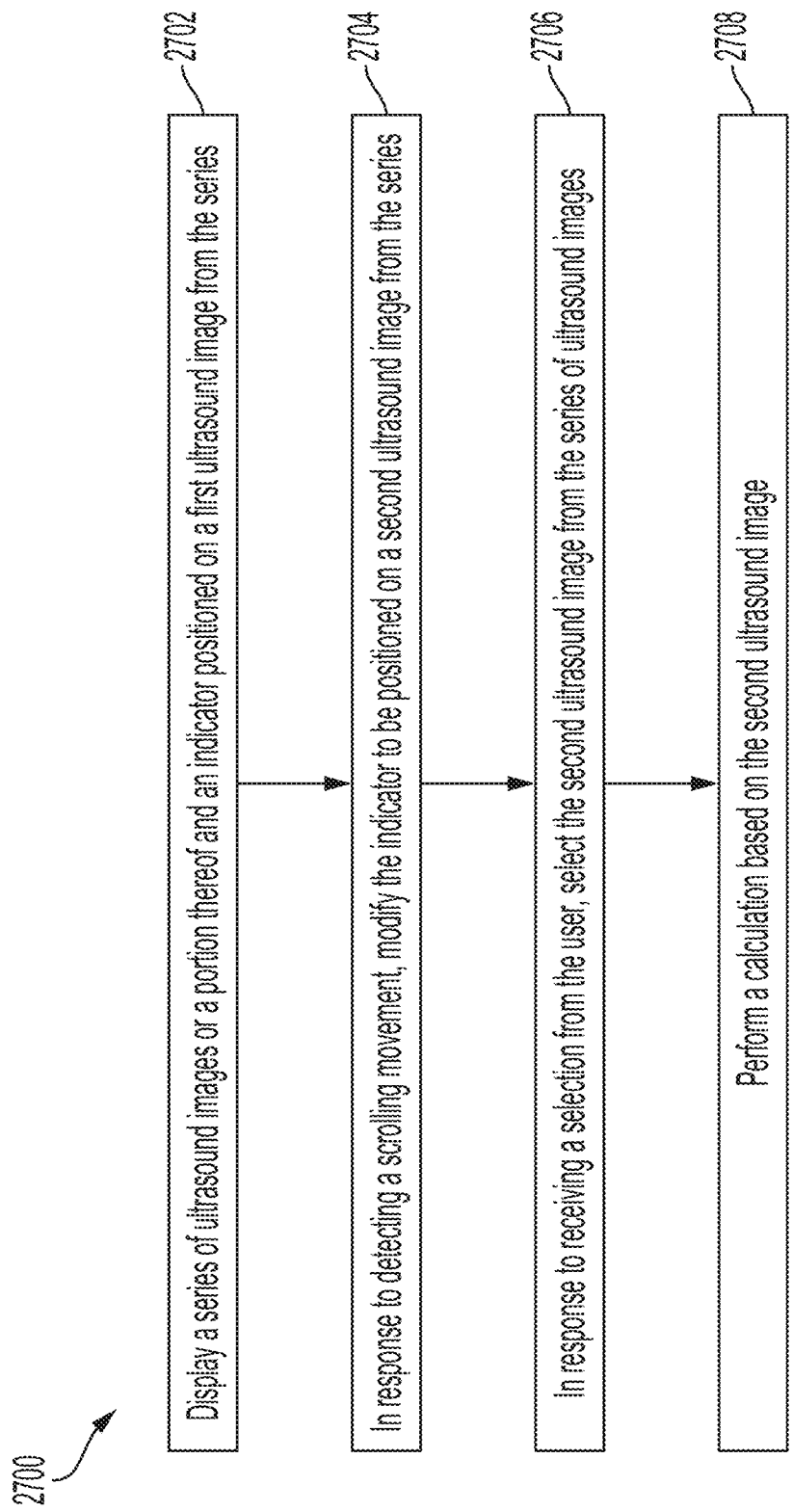
FIG. 27 illustrates an example process for enabling a user to manually modify an input to a calculation performed based at least in part on an ultrasound image, in accordance with certain embodiments described herein.

FIG. 27 illustrates an example process 2700 for enabling a user to manually modify an input to a calculation performed based at least in part on an ultrasound image, in accordance with certain embodiments described herein. The process 2700 is performed by a processing device in operative communication with an ultrasound device.

In act 2702, the processing device a series of ultrasound images (e.g., as the ultrasound image thumbnails 320) or a portion thereof and an indicator (e.g., the current ultrasound image indicator 322) positioned on a first ultrasound image from the series. The series of ultrasound images may be a series collected upon the processing device receiving a selection from the user (e.g., through the automatic calculation option 128) to perform an automatic calculation (e.g., ejection fraction calculation). The first ultrasound image may be an ultrasound image currently selected (e.g., automatically or manually) from the series for use in the calculation, or it may be a default or random ultrasound image from the series (e.g., if no selection has occurred yet). In ejection fraction contexts, the first ultrasound image may be the ultrasound image selected as the end-diastolic or end-systolic ultrasound image. Further description of act 2702 may be found with reference to FIG. 3. The process 2700 proceeds from act 2702 to act 2704.

In act 2704, in response to detecting a scrolling movement, the processing device modifies the indicator to be positioned on a second ultrasound image from the series. Further description of act 2704 may be found with reference to FIGS. 17, 19, 21, and 22. The process 2700 proceeds from act 2704 to act 2706.

In act 2706, in response to receiving a selection from the user (e.g., through the end-diastolic ultrasound image update option 318 or the end-systolic ultrasound image update option 1818), the processing device selects the second ultrasound image from the series of ultrasound images. For example, in ejection fraction contexts, the processing device may select the second ultrasound image as the end-diastolic or end-systolic ultrasound image. The process 2700 proceeds from act 2706 to act 2708.

In act 2708, the processing device performs a calculation (e.g., calculation of ejection fraction) based on the second ultrasound image (e.g., based on the area within a trace on the second ultrasound image). Further description of act 2708 may be found with reference to FIG. 2. In some embodiments, the process 2700 may be repeated to enable a user to manually modify selection of both the end-diastolic and end-systolic ultrasound images.

Figure 28:
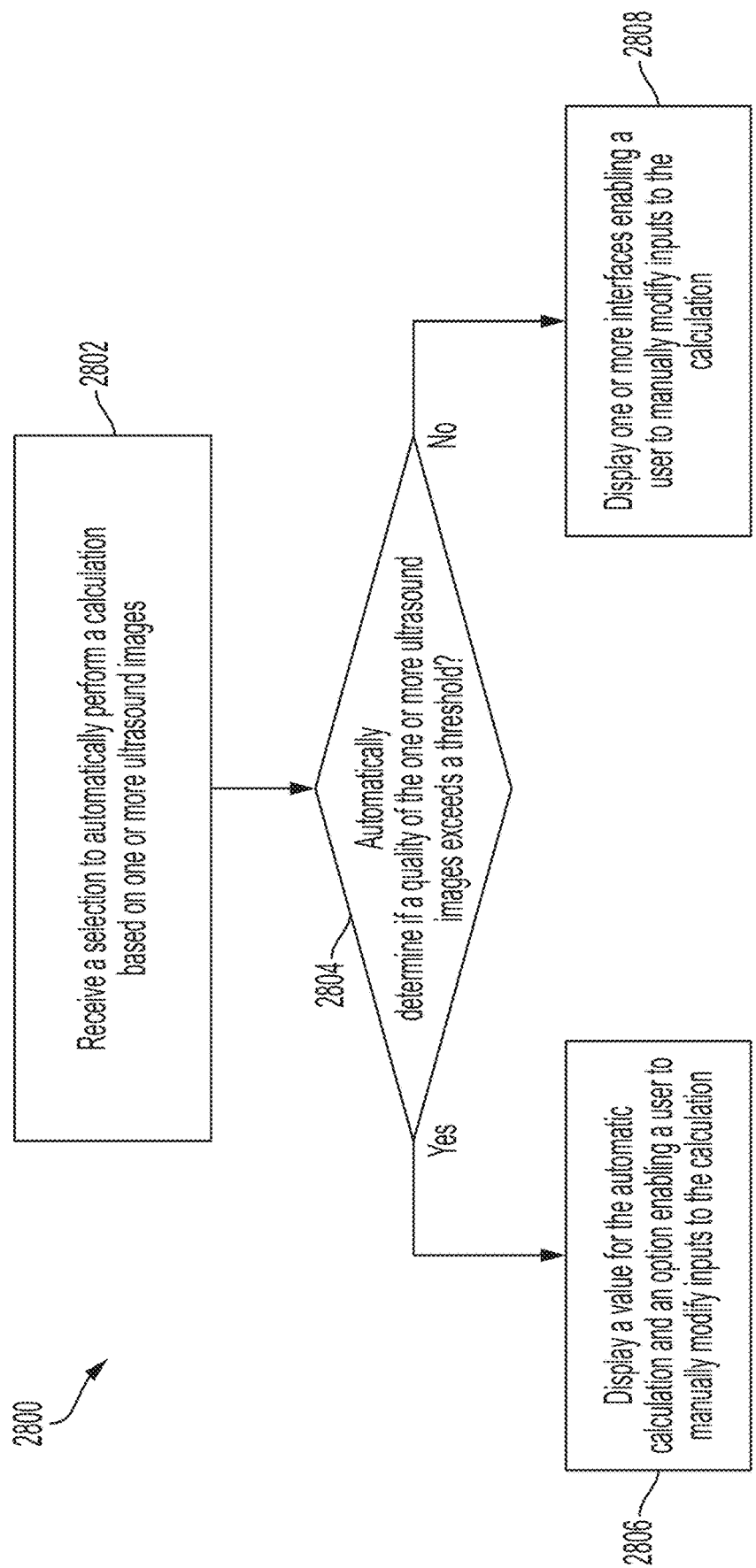
FIG. 28 illustrates an example process for performing a calculation based on one or more ultrasound images, in accordance with certain embodiments described herein.

FIG. 28 illustrates an example process 2800 for performing a calculation based on one or more ultrasound images, in accordance with certain embodiments described herein. The process 2800 is performed by a processing device in operative communication with an ultrasound device.

In act 2802, the processing device receives a selection to automatically perform a calculation based on one or more ultrasound images. For example, the calculation may be calculation of ejection fraction. To receive the selection, the processing device may receive a selection of an option (e.g., the automatic calculation option 128) displayed on a GUI (e.g., the GUI 100). Upon receiving the selection, the processing device may the one or more ultrasound images (e.g., a series of ultrasound images) to a buffer. The process 2800 proceeds from act 2802 to 2804.

In act 2804, the processing device automatically determines if a quality of the one or more ultrasound images exceeds a threshold. The quality may generally be a quality of the one or more ultrasound images for the purpose of automatically performing the calculation. For further description of determining the quality of ultrasound images, see U.S. Provisional Patent Application No. 62/851,502 titled "METHODS AND APPARATUSES FOR ANALYZING IMAGING DATA," filed on May 22, 2019 (and assigned to the assignee of the instant application). If the quality exceeds the threshold, then process 2800 proceeds from act 2804 to act 2806. If the quality does not exceed the threshold, the process 2800 proceeds from act 2804 to act 2808.

Act 2806 occurs if the quality automatically calculated in act 2804 exceeds the threshold. In act 2806, the processing device display a value for the automatic calculation (e.g., an ejection fraction value). For example, the processing device may display the automatic calculation value 206. The processing device also displays an option enabling a user to manually modify inputs to the calculation. For example, the inputs may include selection of one or more particular ultrasound images from a series of ultrasound images and/or definition of traces on one or more ultrasound images. In the ejection fraction context, the option may be, for example, the edit option 236, from which the user may access GUIs such as the GUIs 300, 1700, 1800, and 1900. These GUIs may enable the user to modify selection of the end-diastolic ultrasound image and the end-systolic ultrasound image (e.g., using the ultrasound image thumbnails 320, the current ultrasound image indicator 322, the end-diastolic ultrasound image update option 318, and the end-systolic ultrasound image update option 1818) and to modify traces of the endocardial border of the left ventricle in these ultrasound images (e.g., using the cursors 310, the first icon 314, and the second icon 316).

Act 2808 occurs if the quality automatically calculated in act 2804 does not exceed the threshold. In act 2808, the processing device displays one or more interfaces enabling a user to manually modify inputs to the calculation. For example, the inputs may include selection of one or more particular ultrasound images from a series of ultrasound images and/or definition of traces on ultrasound images. In the ejection fraction context, the interfaces may be, for example, the GUIs 2000, 2100, 2200, and 2300. These GUIs may enable the user to modify selection of the end-diastolic ultrasound image and the end-systolic ultrasound image (e.g., using the ultrasound image thumbnails 320, the current ultrasound image indicator 322, the end-diastolic ultrasound image update option 318, and the end-systolic ultrasound image update option 1818) and to modify traces of the endocardial border of the left ventricle in these ultrasound images (e.g., using the cursors 310, the first icon 314, and the second icon 316).

It should be appreciated that if the quality automatically calculated in act 2804 does not exceed the threshold, the processing device may not automatically generate or select inputs for the calculation (e.g., not select an end-diastolic ultrasound image or an end-systolic ultrasound image) or perform the calculation itself (e.g., not calculate an ejection fraction value) Instead, the processing device displays interfaces from which the user may manually generate or select these inputs. Thus, the user may understand that the calculation is manual and not automatic, as a statistical model may not have confidence in its ability to automatically perform the calculation based on the collected ultrasound images. If the quality automatically calculated in act 2804 does exceed the threshold, the processing device may automatically generate or select inputs for the calculation and perform the calculation itself, but also enable the user to manually modify these inputs if s/he chooses to do so.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Figure 29:
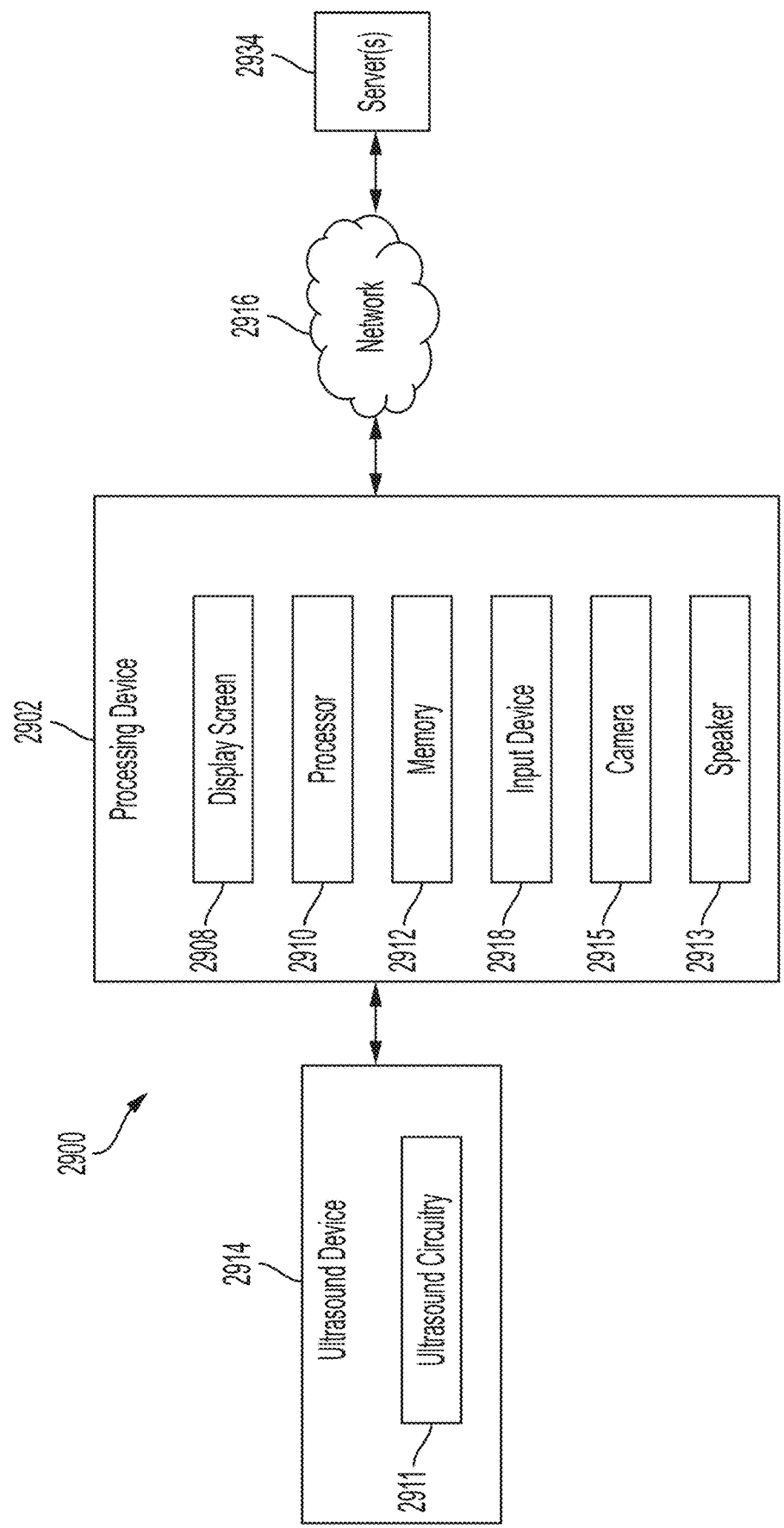
FIG. 29 illustrates a schematic block diagram of an example ultrasound system upon which various aspects of the technology described herein may be practiced.

FIG. 29 illustrates a schematic block diagram of an example ultrasound system 2900 upon which various aspects of the technology described herein may be practiced. The ultrasound system 2900 includes an ultrasound device 2914, a processing device 2902, a network 2916, and one or more servers 2934.

The ultrasound device 2914 includes ultrasound circuitry 2911. The processing device 2902 includes a camera 2915, a display screen 2908, a processor 2910, a memory 2912, an input device 2918, and a speaker 2913. The processing device 2902 is in wired (e.g., through a lightning connector or a mini-USB connector) and/or wireless communication (e.g., using BLUETOOTH, ZIGBEE, and/or WiFi wireless protocols) with the ultrasound device 2914. The processing device 2902 is in wireless communication with the one or more servers 2934 over the network 2916. However, the wireless communication with the processing device 2934 is optional.

The ultrasound device 2914 may be configured to generate ultrasound data that may be employed to generate an ultrasound image. The ultrasound device 2914 may be constructed in any of a variety of ways. In some embodiments, the ultrasound device 2914 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 2911 may be configured to generate the ultrasound data. The ultrasound circuitry 2911 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 2911 (e.g., transmit circuitry, receive circuitry, control circuitry, power management circuitry, and processing circuitry) to form a monolithic ultrasound device. The ultrasound device 2914 may transmit ultrasound data and/or ultrasound images to the processing device 2902 over a wired (e.g., through a lightning connector or a mini-USB connector) and/or wireless (e.g., using BLUETOOTH, ZIGBEE, and/or WiFi wireless protocols) communication link.

Referring now to the processing device 2902, the processor 2910 may include specially-programmed and/or special-purpose hardware such as an application-specific integrated circuit (ASIC). For example, the processor 2910 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 2902 may be configured to process the ultrasound data received from the ultrasound device 2914 to generate ultrasound images for display on the display screen 2908. The processing may be performed by, for example, the processor 2910. The processor 2910 may also be adapted to control the acquisition of ultrasound data with the ultrasound device 2914. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 2902 may be configured to perform certain of the processes (e.g., the processes 2400-2800) described herein using the processor 2910 (e.g., one or more computer hardware processors) and one or more articles of manufacture that include non-transitory computer-readable storage media such as the memory 2912. The processor 2910 may control writing data to and reading data from the memory 2912 in any suitable manner. To perform certain of the processes (e.g., the processes 2400-2800) described herein, the processor 2910 may execute one or more processor-executable instructions stored in one or more non-transitory computer-readable storage media (e.g., the memory 2912), which may serve as non-transitory computer-readable storage media storing processor-executable instructions for execution by the processor 2910. The camera 2915 may be configured to detect light (e.g., visible light) to form an image. The camera 2915 may be on the same face of the processing device 2902 as the display screen 2908. The display screen 2908 may be configured to display images and/or videos, and may be, for example, a liquid crystal display (LCD), a plasma display, and/or an organic light emitting diode (OLED) display on the processing device 2902. The input device 2918 may include one or more devices capable of receiving input from a user and transmitting the input to the processor 2910. For example, the input device 2918 may include a keyboard, a mouse, a microphone, touch-enabled sensors on the display screen 2908, and/or a microphone. The display screen 2908, the input device 2918, the camera 2915, and the speaker 2913 may be communicatively coupled to the processor 2910 and/or under the control of the processor 2910.

It should be appreciated that the processing device 2902 may be implemented in any of a variety of ways. For example, the processing device 2902 may be implemented as a handheld device such as a mobile smartphone or a tablet. Thereby, a user of the ultrasound device 2914 may be able to operate the ultrasound device 2914 with one hand and hold the processing device 2902 with another hand. In other examples, the processing device 2902 may be implemented as a portable device that is not a handheld device, such as a laptop. In yet other examples, the processing device 2902 may be implemented as a stationary device such as a desktop computer. The processing device 2902 may be connected to the network 2916 over a wired connection (e.g., via an Ethernet cable) and/or a wireless connection (e.g., over a WiFi network). The processing device 2902 may thereby communicate with (e.g., transmit data to or receive data from) the one or more servers 2934 over the network 2916. For example, a party may provide from the one or more servers 2934 to the processing device 2902 processor-executable instructions for storing in one or more non-transitory computer-readable storage media (e.g., the memory 2912) which, when executed, may cause the processing device 1704 to perform certain of the processes (e.g., the processes 2400-2800) described herein. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 and published as U.S. Pat. App. Publication No. 2017-0360397 A1 (and assigned to the assignee of the instant application), which is incorporated by reference herein in its entirety.

FIG. 29 should be understood to be non-limiting. For example, the ultrasound system 2900 may include fewer or more components than shown, the ultrasound device 2914 may include fewer or more components than shown, and the processing device 2902 may include fewer or more components than shown.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   a processing device configured to:
   enable a user to manually modify an input to a calculation performed based at least in part on an ultrasound image, wherein the input comprises a selection of an end-diastolic ultrasound image or an end-systolic ultrasound image from a series of ultrasound images, and
   wherein the processing device is configured, when enabling the user to manually modify the input to the calculation, to:
   display the series of ultrasound images or a portion thereof and an indicator positioned on a first ultrasound image from the series;
   in response to detecting a scrolling movement, modify the indicator to be positioned on a second ultrasound image from the series;
   in response to receiving a selection from the user, select the second ultrasound image from the series of ultrasound images as one of the end-diastolic ultrasound image or the end-systolic ultrasound image; and
   perform the calculation based on the second ultrasound image.

2. The apparatus of claim 1, wherein the calculation comprises calculation of ejection fraction.

3. The apparatus of claim 1, wherein the processing device is configured, when enabling the user to manually modify the input to the calculation, to enable the user to manually modify the input to the calculation after the processing device has initially performed the calculation automatically.

4. An apparatus, comprising:
   a processing device configured to:
   enable a user to manually modify an input to a calculation performed based at least in part on an ultrasound image, wherein the input comprises definition of a trace on the ultrasound image and wherein the processing device is configured, when enabling the user to manually modify the input to the calculation, to:
   display the ultrasound image, the trace superimposed on the ultrasound image, and an icon adjacent to the trace;
   in response to detecting a dragging movement that begins on or within a threshold distance of the icon, scale the trace by an amount corresponding to a component of a distance covered by the dragging movement along a long axis of the trace, and rotate the trace by an amount corresponding to a component of the distance covered by the dragging movement perpendicular to the long axis of the trace; and
   perform the calculation based on the manually modified trace.

5. The apparatus of claim 4, wherein the processing device is configured, when enabling the user to manually modify the input to the calculation, to:
   display a second icon adjacent to the trace;
   in response to detecting a second dragging movement that begins on or within a threshold distance of the second icon, translate the trace by an amount in a horizontal direction corresponding to a component of a distance covered by the second dragging movement in the horizontal direction, and translate the trace by an amount in a vertical direction corresponding to a component of the distance covered by the second dragging movement in the vertical direction; and
   perform the calculation based on the manually modified trace.

6. The apparatus of claim 4, wherein the processing device is configured, when enabling the user to manually modify the input to the calculation, to:

display a third icon adjacent to the trace, the third icon corresponding to a point on the trace;

in response to detecting a dragging movement that begins on or within a threshold distance of the third icon, reposition the point at a new location based on the dragging movement that begins on or within the threshold distance of the third icon and redraw the trace such that the trace extends through the new location of the point; and perform the calculation based on the manually modified trace.

7. The apparatus of claim 4, wherein the processing device is configured to generate the trace automatically.

8. The apparatus of claim 4, wherein the trace traces an endocardial border of a left ventricle in the ultrasound image.

9. The apparatus of claim 4, wherein the calculation comprises calculation of ejection fraction.

10. The apparatus of claim 4, wherein the processing device is configured, when enabling the user to manually modify the input to the calculation, to enable the user to manually modify the input to the calculation after the processing device has initially performed the calculation automatically.

11. The apparatus of claim 4, wherein the processing device is configured, when enabling the user to manually modify the input to the calculation, to enable the user to manually modify the definition of the trace after the processing device has initially automatically generated the trace.

\* \* \* \* \*